US006730032B2

(12) United States Patent
Yamauchi

(10) Patent No.: US 6,730,032 B2
(45) Date of Patent: May 4, 2004

(54) ULTRASONIC DIAGNOSTIC DEVICE AND IMAGE PROCESSING DEVICE

(75) Inventor: Masaki Yamauchi, Kadoma (JP)

(73) Assignee: Matsushita Electric Industrial Co., Osaka (JP)

( * ) Notice: Subject to any disclaimer, the term of this patent is extended or adjusted under 35 U.S.C. 154(b) by 57 days.

(21) Appl. No.: 10/087,811

(22) Filed: Mar. 5, 2002

(65) Prior Publication Data

US 2002/0123688 A1 Sep. 5, 2002

(30) Foreign Application Priority Data

Mar. 5, 2001 (JP) ....................................... 2001-059708

(51) Int. Cl.[7] ................................................. A61B 8/00
(52) U.S. Cl. ....................................... 600/443; 128/916
(58) Field of Search ........................ 600/437, 440–441, 600/443, 447, 453–456; 128/916

(56) References Cited

U.S. PATENT DOCUMENTS 5,551,434 A * 9/1996 Iinuma ....................... 600/455
6,139,500 A * 10/2000 Clark ......................... 600/443

* cited by examiner

Primary Examiner—Francis J. Jaworski
(74) Attorney, Agent, or Firm—Wenderoth, Lind & Ponack, L.L.P.

(57) ABSTRACT

A control unit (116) resets a time stamp value whenever a pulsation is detected. In accordance with an electric signal from an ultrasonic search unit (101) and a send/receive unit (102), the image generating unit (110) generates ultrasound image data, attaches a time stamp to the generated image data, and places it into a data storing unit (112). A contour extracting unit (113) extracts a contour within the image data stored in the data storing unit (112), generates contour data, and attaches the same time stamp as the stamp attached to the image data to the contour data. An interpolated data generating unit (114) interpolates between the contour data in accordance with the attached time stamp to generate contour data corresponding to times at which sampling was not performed. A volume calculating unit (115) calculates a left ventricular volume (LVV) of a heart from the interpolated contour data according to the Modified Simpson method.

21 Claims, 18 Drawing Sheets

THE MODIFIED SIMPSON METHOD

RADIUSES Ai AND Bi OF SLICES OF TWO CROSS SECTIONS THAT ARE ORTHOGONAL TO EACH OTHER, AND INTERVAL h BETWEEN SLICES

⇩

VOLUME (OR CAPACITY) $V = \Sigma AiBi \times h\pi$

CROSS SECTIONS THAT SHARE
AXIS $\ell$ AND ARE ORTHOGONAL TO EACH OTHER

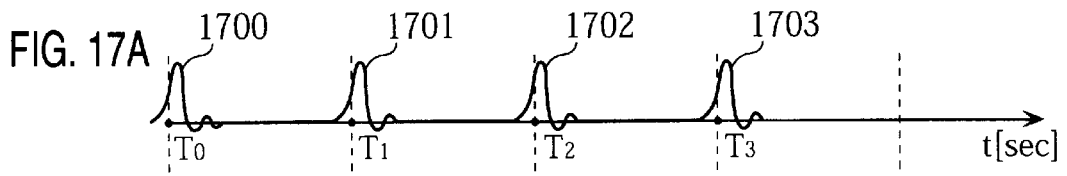
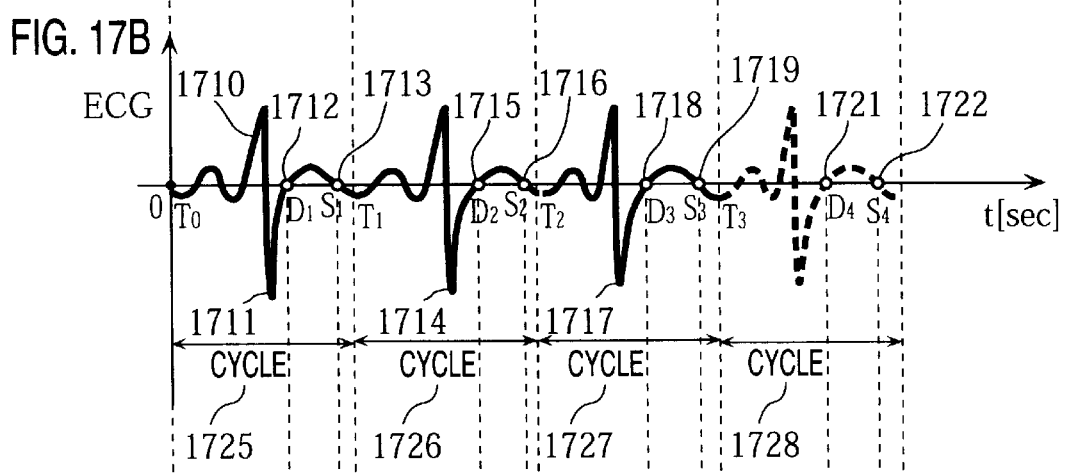
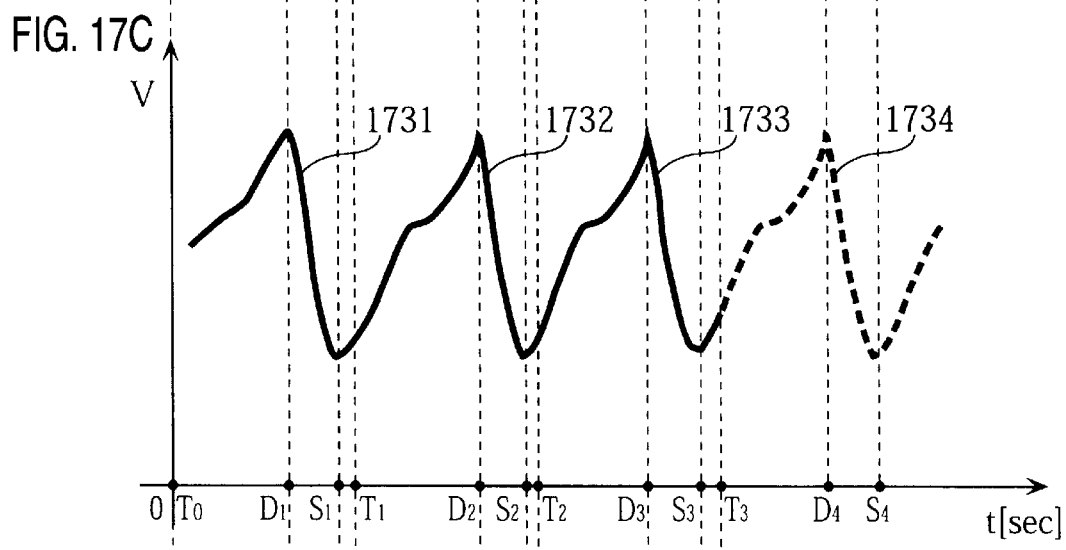
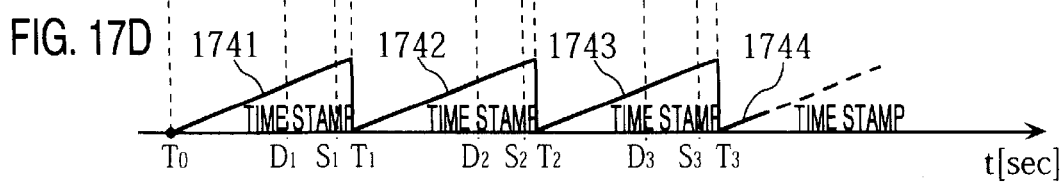

ULTRASONIC DIAGNOSTIC DEVICE AND IMAGE PROCESSING DEVICE

BACKGROUND OF THE INVENTION

1. Field of the Invention

The present invention relates to an ultrasonic diagnostic device and an image processing device, and particularly to a technique for improving a time resolution of a sequence of ultrasound images obtained at a predetermined frame rate.

2. Description of Background Art

An ultrasonic diagnostic device receives an echo obtained when ultrasound emitted from an ultrasonic probe is partially reflected on reflection points and surfaces of tissue of an object of a living body to be examined. The ultrasonic diagnostic device then performs signal processing for the received echo, and generates an ultrasound image (an echo image) for the examined object. Since the ultrasonic diagnostic device generates a two-dimensional (2D) ultrasound image of an examined object of a soft part and the like without invasion, it is widely used as a device which performs examination with high level of safety, and therefore is essential in fields such as clinical medicine.

As digital ultrasonic diagnostic devices are in increasingly widespread use, a variety of ultrasonic examinations are conducted with them.

For instance, an ultrasonic diagnostic device continuously samples ultrasound images of an examined object over a predetermined time and accumulates them to allow the operator to later closely examine a sequence of these ultrasound images and their physical quantity, such as movement of the object, and use obtained information for diagnosis.

For closely examining constantly changing movement of the object such as a heart and a circulatory organ, however, the present frame rate (e.g., 10 frames/second (fps)) used by an ultrasonic diagnostic device is not sufficient.

Methods considered to solve this problem include a method for raising a frame rate of sampling by reducing a total number of pixels constituting each ultrasound image, and density resolution of each pixel, and a method for omitting real-time processing from signal and image processing. These methods, however, reduce information amount of each ultrasound image, and so cannot improve accuracy of examination as a whole.

There is also a new technique of accurate examination by the use of an ultrasonic diagnostic device, which uses ultrasound images corresponding to different cross sections (such as a two-chamber view and a four-chamber view) of the same object (such as a heart). These ultrasound images have been generated in the same phase in a pulsation (i.e., relatively the same time in a pulsation cycle), so that examination with increased accuracy can be performed (see Japanese Patent Application No. 2001-23819).

With this technique, ultrasound images in the same phase are extracted from different sequences of ultrasound images. However, there are not always ultrasound images in the same phase within these sequences because timing with which these ultrasound images have been sampled and generated may differ from one another.

Consequently, ultrasound images generated in different phases are used as ultrasound images in the same phase, but such difference in phase results in decreasing accuracy of examination.

SUMMARY OF THE INVENTION

The present invention is made in view of the above problems, and aims to achieve the following three objects.

As the first object, the present invention aims to provide an ultrasonic diagnostic device and an image processing device capable of examination with increased accuracy by increasing an apparent sampling rate applied to an ultrasound image they generates without sacrificing a resolution of the ultrasound image and real-time performance.

As the second object, the present invention aims to provide an ultrasonic diagnostic device and an image processing device capable of examination with increased accuracy even when the devices use two or more ultrasound image sequences that have been generated in different phases as a result of difference in their sampled times.

As the third object, the present invention aims to provide an ultrasonic diagnostic device and an image processing device capable of accurately examining an object (such as a left ventricle (LV) of a heart) whose information (such as that showing a left ventricular volume (LVV)) used for diagnosis changes over time. To achieve this, the ultrasonic diagnostic device and the image processing device generate an ultrasound image corresponding to an predicted time at which the diagnostic information takes a characteristic value.

For achieving the first object, the ultrasonic diagnostic device and the image processing device generate ultrasound images through sampling, associates each of the generated ultrasound image with a time stamp, and interpolates between data of the ultrasound image to generate image data corresponding to a time at which the sampling was not performed.

The second object can be achieved by normalizing a cycle for ultrasound image data in accordance with time stamps associated with the ultrasound image data, and then performs the above interpolation between the ultrasound image data corresponding to the normalized cycle.

The third object can be achieved by predicting a time at which a left ventricular volume (LVV) becomes a minimum or a maximum, and generates an ultrasound image at the predicted time.

In more detail, the above objects can be achieved by an ultrasonic diagnostic device that generates and displays an ultrasound image containing an image of an object which is subject to examination in accordance with reflection of ultrasound. This ultrasonic diagnostic device includes: an image generating unit for successively generating an ultrasound image; a quantity extracting unit for extracting a characteristic quantity related to the object within the generated ultrasound image; a time stamp generating unit for generating a time stamp indicating a time at which the ultrasound image has been generated, and associating the time stamp with the extracted characteristic quantity to make a pair; an interpolating unit for performing interpolation using a plurality of pairs made by the time stamp generating unit so as to generate new characteristic quantities corresponding to times other than times indicated by time stamps contained in the plurality of pairs; an information generating unit for generating diagnostic information on the object in accordance with the new characteristic quantities; and a display unit for displaying the generated diagnostic information.

The above interpolation on characteristic quantities generates new characteristic quantities that each correspond to a time at which sampling was not performed, and diagnostic information based on such characteristic quantities can be generated. Consequently, the above ultrasonic diagnostic device can achieve examination with higher accuracy than conventional examination using the same frame rate as the present examination. In addition, since such highly accurate examination can be achieved by data processing such as interpolation of characteristic quantity, it costs lower than other method which increases a maximum frame rate.

Here, the above ultrasonic diagnostic device may further include: a pulsation detecting unit for detecting every pulsation related to the object; and a clock unit for measuring an elapsed time from the detection of each pulsation. Here, a time indicated by each time stamp may be an elapsed time measured by the clock unit.

For this construction, a value of the time stamp is incremented in synchronization with a pulsation of the object. This allows different sets of data that have been generated in the same phase in a pulsation cycle to be specified out of sets of data obtained at different times. Consequently, with the present diagnostic device, movements of the living body can be examined from a variety of viewpoints in synchronization with pulsations.

Here, for the above ultrasonic diagnostic device, the interpolating unit may (a) superimpose a plurality of characteristic quantities over one another within a single pulsation cycle, the plurality of characteristic quantities having been extracted over a plurality of pulsation cycles, and (b) perform the interpolation between the superimposed characteristic quantities to generate the new characteristic quantities.

For this construction, characteristic quantities over two or more pulsation cycles are normalized before interpolation. This reduces an examination error resulting from abnormal movements of the living body, signal noise, and dispersion in values of the examination.

Here, with the above ultrasonic diagnostic, before superimposing the plurality of characteristic quantities over one another, the interpolating unit may normalize the plurality of pulsation cycles to generate the single pulsation cycle by correcting time stamps associated with the plurality of characteristic quantities.

For this construction, different pulsation cycles are corrected to a pulsation cycle of the same duration, and characteristic quantities are superimposed over one another based on this corrected pulsation cycle without a phase of each characteristic quantity changed before and after the superimposition. Accordingly, highly accurate diagnostic information can be obtained.

Here, for the above ultrasonic diagnostic device, the interpolating unit may perform the interpolation using the plurality of pairs that each contain a time stamp and a characteristic quantity related to an ultrasound image in first sectional view so as to generate new characteristic quantities related to the first sectional view. The information generating unit may include: an intersecting data obtaining unit for obtaining a characteristic quantity related to an ultrasound image in second sectional view from the quantity extracting unit, and obtaining a time stamp associated with the obtained characteristic quantity from the time stamp generating unit, the first and second sectional views intersecting at a predetermined view; a data specifying unit for specifying a characteristic quantity out of the new characteristic quantities related to the first sectional view, the specified characteristic quantity being associated with a time stamp that indicates a same time as the time stamp obtained by the intersecting data obtaining unit; and a data generating unit for generating the diagnostic information by using the specified characteristic quantity and the obtained characteristic quantity.

With this construction, the diagnostic information is produced from ultrasound images in the intersecting first and second sectional views, which have been generated at different periods. This generates a characteristic quantity that is closer to an actual characteristic quantity of the object than a characteristic quantity obtained merely from an ultrasound image in a single sectional view. As a result, accurate examination can be achieved.

Here, with the above ultrasonic diagnostic device, the intersecting data obtaining unit may also perform interpolation using a plurality of pairs that each contain: (a) a characteristic quantity related to the second sectional view; and (b) a time stamp associated with the characteristic quantity, and generate a new characteristic quantity related to the second sectional view. The data specifying unit may specify a characteristic quantity related to the first sectional view, the specified characteristic quantity being associated with a time stamp indicating a same time as a time stamp associated with the new characteristic quantity related to the second sectional view.

With this construction, interpolation is performed between not only ultrasound images in the first sectional view but also ultrasound images in the second sectional view, and the diagnostic information is generated based on characteristic quantities for which such interpolations have been performed. This allows diagnostic information to be generated at shorter intervals, and therefore a peak position in a change curve, for instance, can be accurately obtained.

Here, with the above ultrasonic diagnostic device, each time the image generating unit generates an ultrasound image in the second sectional view, the data generating unit may generate diagnostic information. Each time the diagnostic information is generated, the display unit may display the diagnostic information.

For this construction, the diagnostic information is generated whenever an ultrasound image in the second sectional view is sampled, which achieves real-time diagnosis for which diagnostic information is instantaneously provided.

Here, the above ultrasonic diagnostic device may also include a volume specifying unit for specifying a maximum and a minimum of the volume in a pulsation cycle by using the volume shown in the diagnostic information.

For this construction, maximum and minimum values in each pulsation cycle are displayed. This can therefore provide, for example, useful information such as an end-diastolic LVV and an end-systolic LVV of the heart.

The above objects can be also achieved by an ultrasonic diagnostic device that generates and displays an ultrasound image containing an image of an object which is subject to examination in accordance with reflection of ultrasound. The ultrasonic diagnostic device includes: a signal receiving unit for receiving an electrocardiogram (ECG) signal related to the object; an end-time predicting unit for predicting at least one of an end-diastolic time and an end-systolic time from at least one of a past end-diastolic time and a past end-systolic time that the end-time predicting unit has specified using the received ECG signal; and an image generating unit for generating an ultrasound image at the at least one of the predicted times.

With this construction, future end-diastolic and end-systolic times can be predicted from past end-diastolic and end-systolic times, which have been specified using the action potential signal. An ultrasound image is then generated at the predicted times. As a result, a more accurate LVV of the heart in end-diastolic and end-systolic times can be calculated.

Here, the above objects can be also achieved by an ultrasonic diagnostic device that generates and displays an ultrasound image containing an image of an object which is subject to examination in accordance with reflection of ultrasound. This ultrasonic diagnostic device includes: an information calculating unit for calculating diagnostic information from the ultrasound image; a time predicting unit for predicting a time at which the calculated diagnostic information takes a characteristic value by using the diagnostic information; and an image generating unit for generating an ultrasound image for the object at the predicted time.

The above ultrasonic diagnostic device predicts a time at which the calculated diagnostic information takes a characteristic value by using past diagnostic information. The diagnostic device then generates an ultrasound image at the predicted time. This can achieve examination with increased accuracy in accordance with diagnostic information corresponding to the predicted time and times around the predicted time.

In order to achieve the above objects, the present invention may be embodied as an image processing device that includes the above units of the ultrasonic diagnostic device, or as a program including steps of units characteristic to the diagnostic device. Such program may be stored in not only ROM (read only memory) used by the ultrasonic diagnostic device and the image processing device but also a recording medium, such as a CD-ROM disc, to be distributed. The program may be also distributed via a communication network and other transmission media.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIG. 17 is used to explain an end-time prediction function of a control unit in the ultrasonic diagnostic device shown in FIG. 16.

DESCRIPTION OF THE PREFERRED EMBODIMENTS

The following describes the present invention by using several embodiments and drawings.

First Embodiment

Figure 1:
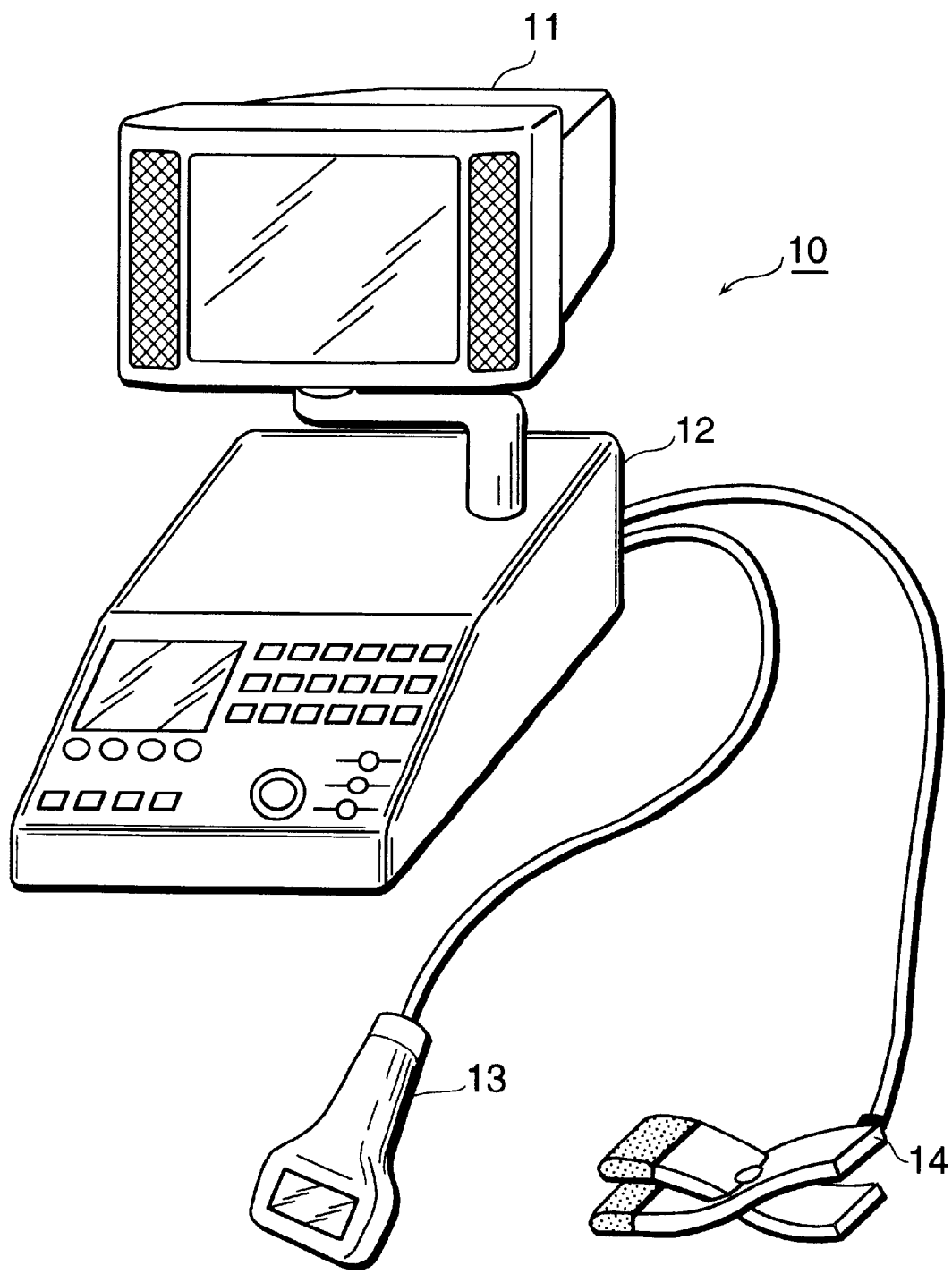
FIG. 1 shows external view of an ultrasonic diagnostic device according to the first embodiment of the present invention.

FIG. 1 shows an ultrasonic diagnostic device 10 in external view according to the present embodiment. This ultrasonic diagnostic device 10 is capable of not only generating an ultrasound image but also measuring and displaying change in volume of an object, particularly a left ventricle (LV) of a heart, in a cardiac cycle to diagnose function of the heart. The ultrasonic diagnostic device 10 comprises a display apparatus 11, a main unit 12, a probe 13, and a pulsation sensor 14.

The display apparatus 11 is achieved by a liquid crystal display (LCD), a cathode-ray tube (CRT), or the like which displays information and an ultrasound image obtained according to an echo method, and includes a touch panel and the like that receive an input from an operator.

The main unit 12 includes the following elements: a send/receive circuit that controls transmission/reception of ultrasound via the probe 13; a signal/image processing circuit containing a digital signal processor (DSP) and random access memory (RAM) for processing images and signals of various types; a group of switches and a mouse for receiving the operator's operation; and an LCD unit containing a touch panel. The main unit 12 also generates a pulsation pulse based on an electric signal from the pulsation sensor 14.

The probe 13 is a search unit containing an ultrasonic oscillator and an acoustic lens for receiving and sending ultrasound. The probe 13 includes an LCD panel that displays data such as a left ventricular volume (LVV) to be examined.

The pulsation sensor 14 detects a pulsation (either a heartbeat or a pulse) of a patient via a pressure sensor, converts the detected pulsation into an electric signal, and sends the electric signal to the main unit 12.

Figure 2:
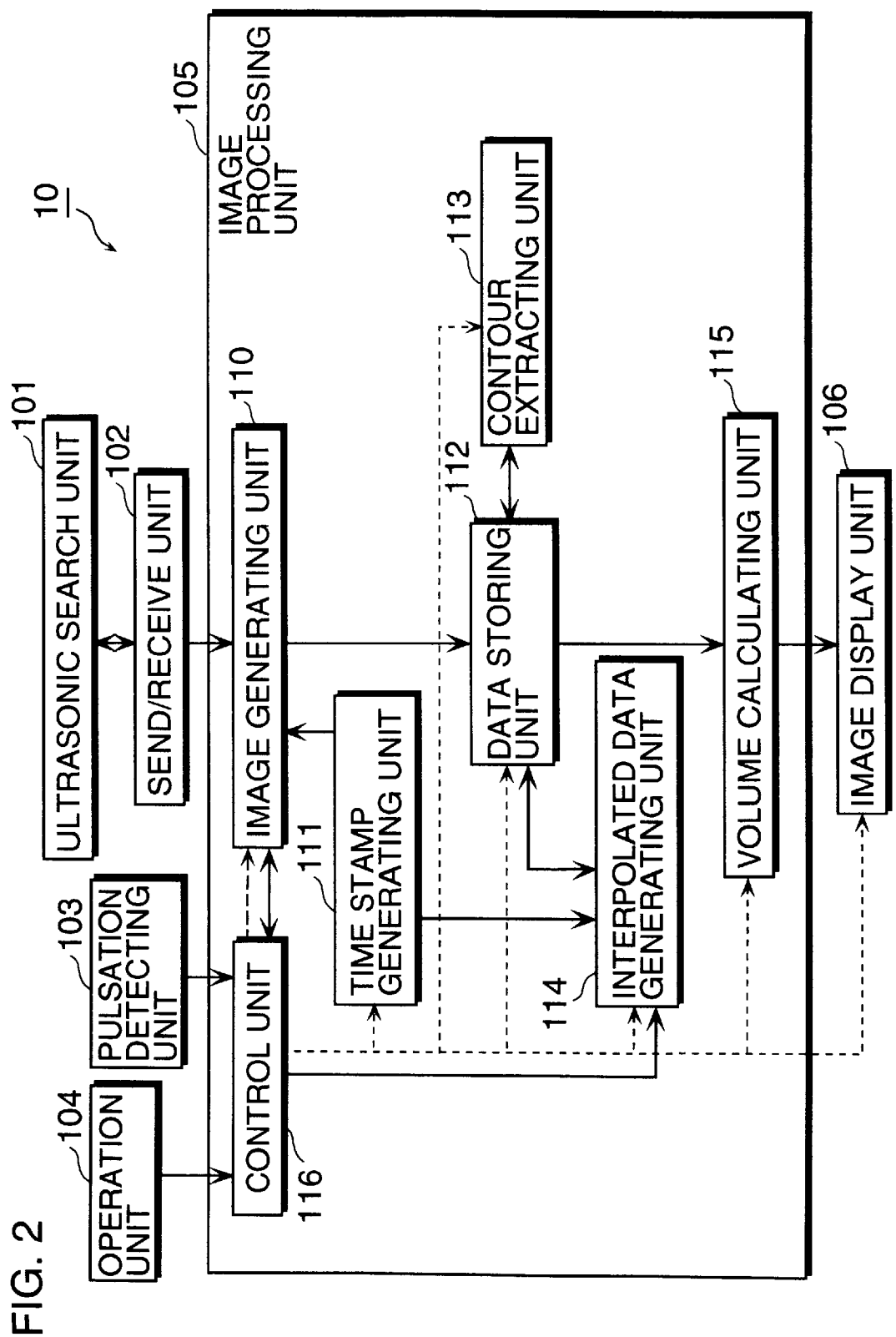
FIG. 2 is a block diagram showing a main function configuration of the ultrasonic diagnostic device in FIG. 1.

FIG. 2 is a block diagram showing a main function configuration of the ultrasonic diagnostic device 10. This diagnostic device 10 includes an ultrasonic search unit 101, a send/receive unit 102, a pulsation detecting unit 103, an operation unit 104, an image processing unit 105, and an image display unit 106.

The ultrasonic search unit 101 corresponds to the probe 13 shown in FIG. 1, and may be a probe that performs electronic scan based on the phased array method. The ultrasonic search unit 101 receives a control signal from the send/receive unit 102, and emits ultrasound (e.g., ultrasonic pulse) in accordance with this control signal. The search unit 101 also receives ultrasound (hereafter called ultrasonic echo) reflected from inside the living body of the patient, converts the ultrasonic echo into an electric signal, and sends it to the send/receive unit 102.

The send/receive unit 102 is achieved by a sender/beam former for having the ultrasonic search unit 101 generate ultrasound and by a receiver/beam former for receiving an electric signal from the search unit 101 that has detected an ultrasonic echo. The send/receive unit 102 processes the received electric signal such as by amplifying it, and sends the processed electric signal to the image processing unit 105.

The pulsation detecting unit 103 corresponds to the pulsation sensor 14 shown in FIG. 1. The pulsation detecting unit 103 detects a pulsation of the patient, converts it to an electric signal, and sends the signal to the control unit 116.

The operation unit 104 receives an input from the operator via a switch, a touch panel, or the like, and sends a control signal corresponding to the received input to the image processing unit 105.

In accordance with the electric signal from the send/receive unit 102, the image processing unit 105 generates an ultrasound image, extracts a contour of the object from the ultrasound image, and calculates a volume of the object in accordance with the extracted contour. The image processing unit 105 performs the following characteristic operations to accurately calculate an LVV of the heart in particular.

(i) Volume calculation based on not a single ultrasound image but ultrasound images of two types (i.e., two- and four-chamber views of the LV for the present embodiment).

(ii) Generating a time stamp in synchronization with a pulsation, and attaching a time stamp to each ultrasound image so as to specify ultrasound images in two- and four-chamber view which have been generated in the same phase in a pulsation cycle (in other words, the two types of chamber views correspond to relatively the same time). Performing interpolation (relative to time) on ultrasound images (or characteristic quantity obtained from the ultrasound images) in accordance with values of time stamps attached to the ultrasound images.

Figure 3:
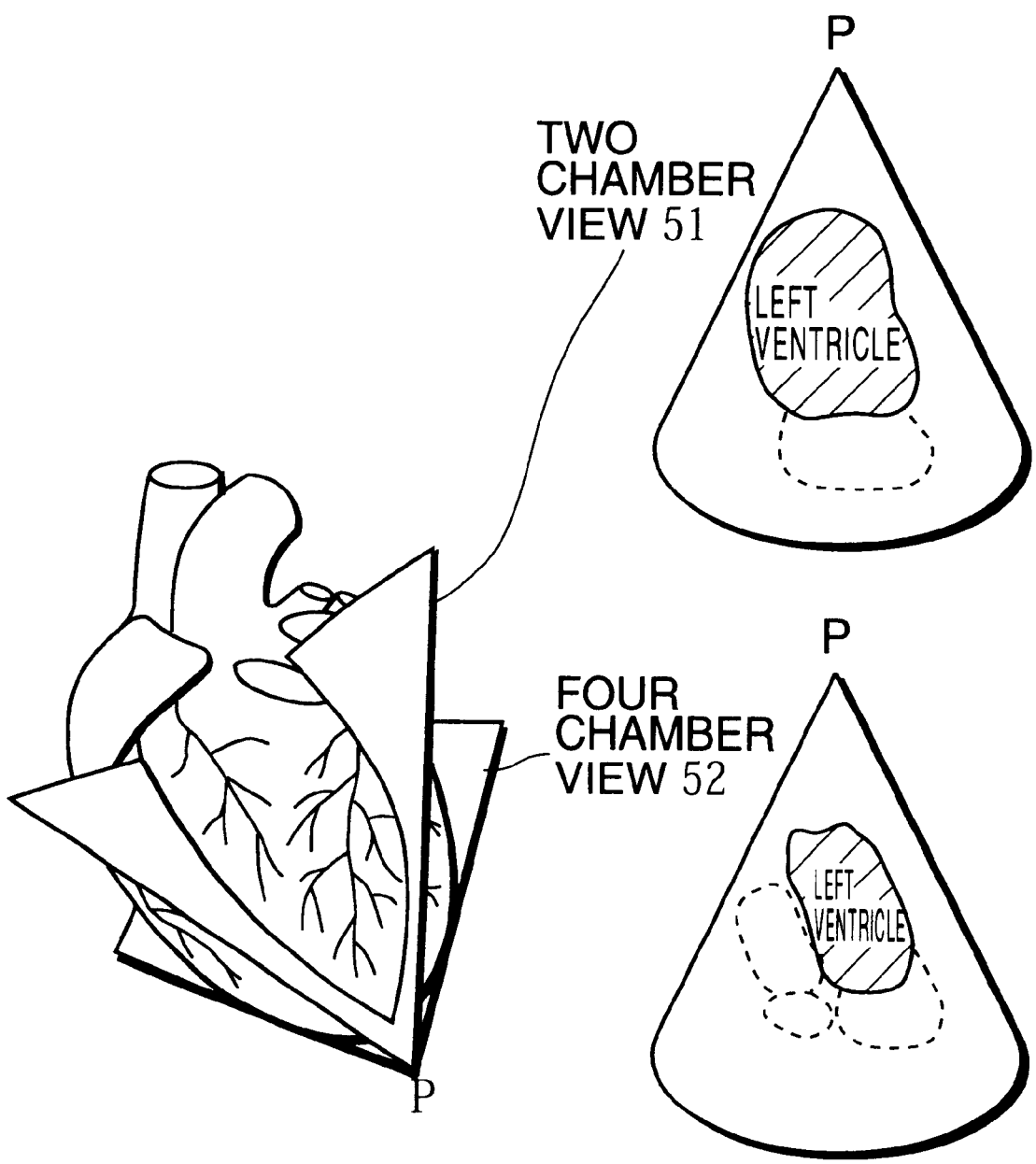
FIG. 3 is used to explain a two-chamber view and a four-chamber view.

As shown in FIG. 3, the two-chamber view includes an LV, a left atrium, and an apex "P" of the heart, and the four-chamber view includes these and a right ventricle and a right atrium. The two- and four-chamber views intersect at a predetermined angle (e.g., 90 or 120 degrees).

To achieve the above characteristic operations, the image processing unit 105 includes an image generating unit 110, a time stamp generating unit 111, an data storing unit 112, a contour extracting unit 113, an interpolated data generating unit 114, a volume calculating unit 115, and a control unit 116.

The time stamp generating unit 111 includes an internal basic clock such as a 42-MHz clock, and resets a counter value as a time stamp value whenever it receives, from the control unit 116, a notification which indicates that a pulsation is detected. Until the time stamp generating unit 111 receives the next notification indicating the detection, the stamp generating unit 111 continues to monotonously increment the counter value.

The image generating unit 110 starts receiving an electric signal from the send/receive unit 102 with timing instructed by the control unit 116. The image generating unit 110 then performs analog-to-digital (A/D) conversion on the received electric signal to generate image data. Whenever it generates the image data, the image generating unit 110 reads a time stamp from the time stamp generating unit 111, attaches the time stamp to this image data, and sends them to the data storing unit 112.

The above "image data" refers to data such as two-dimensional (2D) density data. The image data is generated each time the ultrasonic search unit 101 performs one scan, and displayed in B mode. A data size of such image data can be calculated as 3.2 MB (megabytes) according to an expression below when the image data is generated by sampling at a sampling rate of 10 fps for 5 seconds and consists of 256×256 pixels/frame with a resolution of 8 bits/pixel.

$$10(\text{fps}) \times 5(\text{sec}) \times 256 \times 256(\text{pixels}) \times 8 \text{ bits} = 3.2 \text{ MB}$$

The data storing unit 112 stores the image data having the time stamp sent from the image generating unit 110. In accordance with instructions from the contour extracting unit 113 and the interpolated data generating unit 114, the data storing unit 112 sends stored image data to the extracting unit 113 and the data generating unit 114, respectively. The data storing unit 112 also receives image data and contour data (which may be interpolated) from the interpolated data generating unit 114 and the extracting unit 113, and stores them.

Here, the above "contour data" refers to data containing the following data: coordinate data showing X and Y coordinates of a plurality of pixels that make up the extracted contour; and calculation data used to approximately calculate volume of the object indicated by the extracted contour. When the approximate calculation is performed according to the Modified Simpson method (described below), this calculation data may show a radius of a slice related to the extracted contour, and an interval between such slices.

The data storing unit 112 also stores parameters related to an interpolation method (such as that using linear interpolation, or a B-spline) which is set by the operator in advance. For instance, the stored parameters indicate that interpolation for a radius of a slice is performed using a B-spline (that passes N points and has the order of "K−1") and that interpolation for image data is based on linear interpolation. Such parameters can be changed by the operator as necessary.

The contour extracting unit 113 receives the image data from the data storing unit 112, and extracts a contour of the object such as the LV of the heart within the image data in accordance with this image data. The contour extracting unit 113 then generates contour data and sends it to the data storing unit 112. The contour data generated here contains a time stamp that has the same value as the image data from which the contour data is extracted. A detailed description of a method for extracting a contour by using image data is disclosed by Japanese Patent Application No. 2001-23819.

Figure 4:
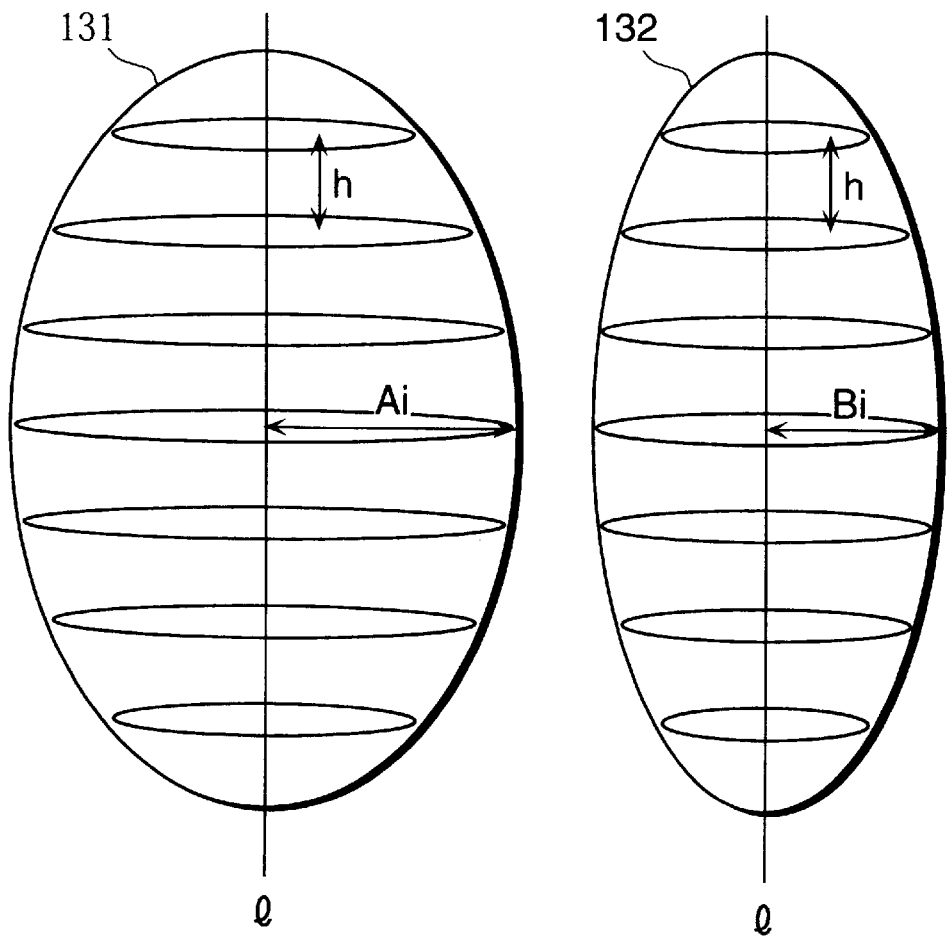
FIG. 4 is used to explain a radius of a slice and an interval between such slices, which are examples of calculation data contained in contour data.

FIG. 4 illustrates examples of a radius of a slice and an interval between such slices, which are part of the above calculation data used in accordance with the Modified Simpson method. More specifically, this drawing shows a contour 131 in a two-chamber image of the LV of the heart, and a contour 132 in a four-chamber image of the same LV. These contours 131 and 132 are extracted from image data of the two- and four-chamber views that intersect (at 90 degrees, for instance). The figure also shows radiuses "Ai" and "Bi" ("i"=1~7 for this figure) of slices and an interval "h" between such slices, which are calculation data either specified or calculated from the two contours 131 and 132. When this calculation data (i.e., radiuses "Ai" and "Bi", and an interval "h") is substituted into the shown approximate expression, a volume "V" of the LV is calculated.

In accordance with image data generated by the image data generating unit 110, the interpolated data generating unit 114 interpolates either image data or calculation data corresponding to time at which sampling is not performed. This interpolation generates sets of data arranged at shorter intervals than data prior to interpolation. The sets of data generated by this interpolation may have a time resolution of, for instance, 0.1 milliseconds (msec). More specifically, in accordance with image data after contour extraction, the interpolated data generating unit 114 interpolates 2D density data and values of the above radiuses "Ai" and "Bi" corresponding to time at which sampling is not performed.

The volume calculating unit 115 calculates a volume of the object (the LV) by using the calculation data and the approximate expression (such as that according to the Modified Simpson method shown in FIG. 4).

The control unit 116 is achieved, for instance, by a microcomputer containing ROM and RAM (random access memory), and controls timing of operations of other units in the image processing unit 105. In more detail, on detecting a rise in the pulsation pulse via the pulsation detecting unit 103, the control unit 116 instructs the time stamp generating unit 111 to reset a value of a time stamp. When an operator's input indicating interpolation is received, the control unit 116 sends parameters relating to a method for the interpolation, and pulsation cycle data to the interpolated data generating unit 114. This pulsation cycle data is used to specify an interpolation range (i.e., one or more successive pulsation cycles for which interpolation should be performed) designated by the operator.

The above "pulsation cycle data" indicates the following information: a total number (e.g., "3") of pulsations contained in the interpolation range; a pulsation number (e.g., "No. 3") assigned to the first pulsation cycle within the interpolation range; and each pulsation cycle associated with a pulsation number (which may be shown as "No. 3: 0.98[sec]", "No. 4: 1.00[sec]", and "No. 5: 1.03[sec]") within the interpolation range.

The image display unit 106 presents an ultrasound image generated by the image processing unit 105 in B mode and measurement information, such as the LVV, onto the LCD unit and the LCD panel of the probe 13. The image display unit 106 is achieved by elements such as a graphic accelerator and a scan converter.

Figure 5:
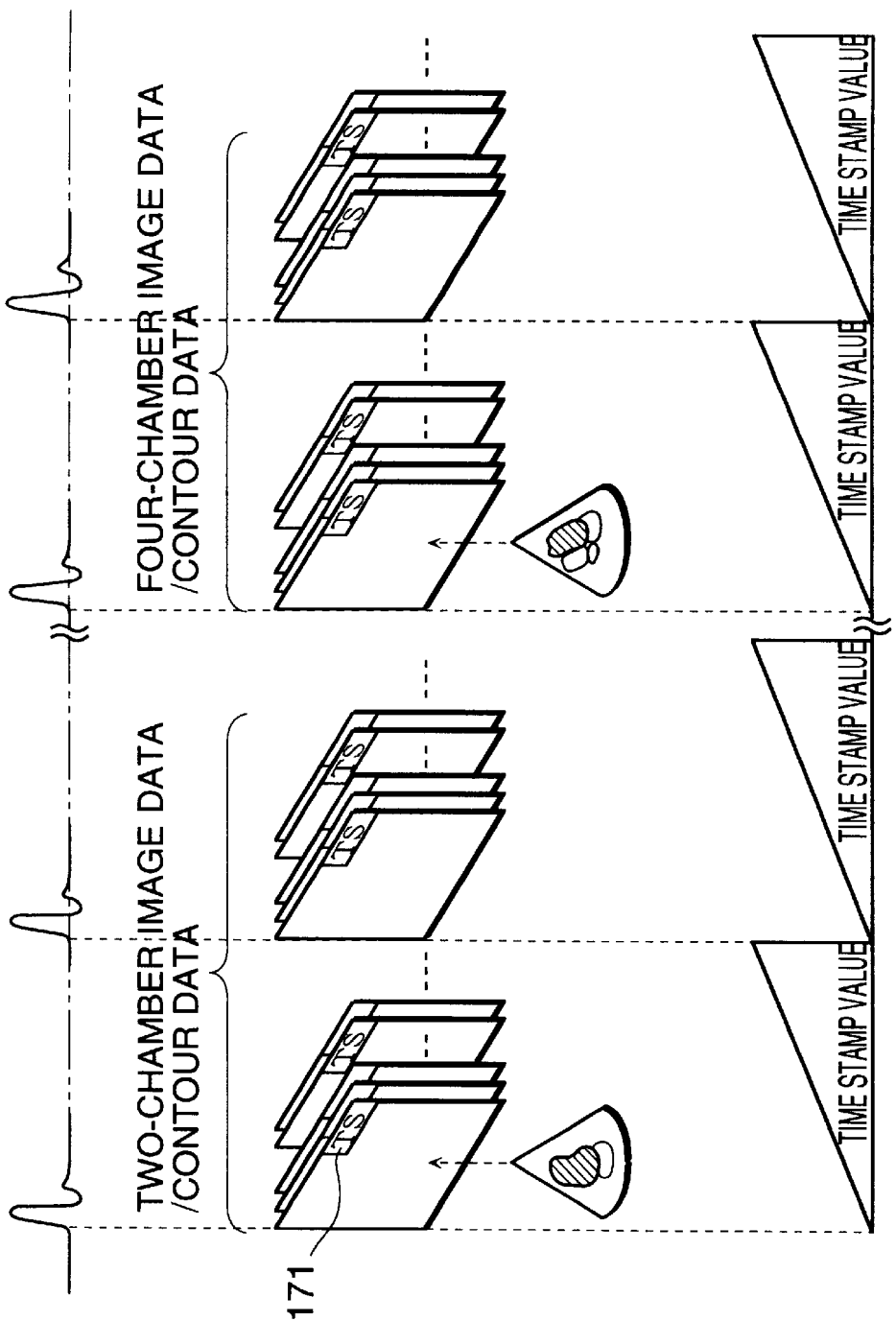
FIGS. 5A–5C show representation of image data and contour data stored in a data storing unit of the above ultrasonic diagnostic device.

FIGS. 5A–5C show representation of image data and contour data for two- and four-chamber images stored in the data storing unit 112. More specifically, FIG. 5A shows a waveform of a pulsation pulse, FIG. 5B shows representation of image data and contour data of the two- and four-chamber images, and FIG. 5C shows representation of a state in which a value of a time stamp monotonously increases.

As shown in FIG. 5B, image data and contour data of the two types of chamber views are given a time stamp 171 that corresponds to a time at which the respective data has been sampled, and placed into the data storing unit 112. As shown in FIG. 5C, a time stamp is reset as soon as the pulsation pulse rises. A value of the time stamp 171 thereafter continues to increase monotonously until the next pulse rise is detected. The time stamp generating unit 111 thus controls the time stamp 171.

Figure 6:
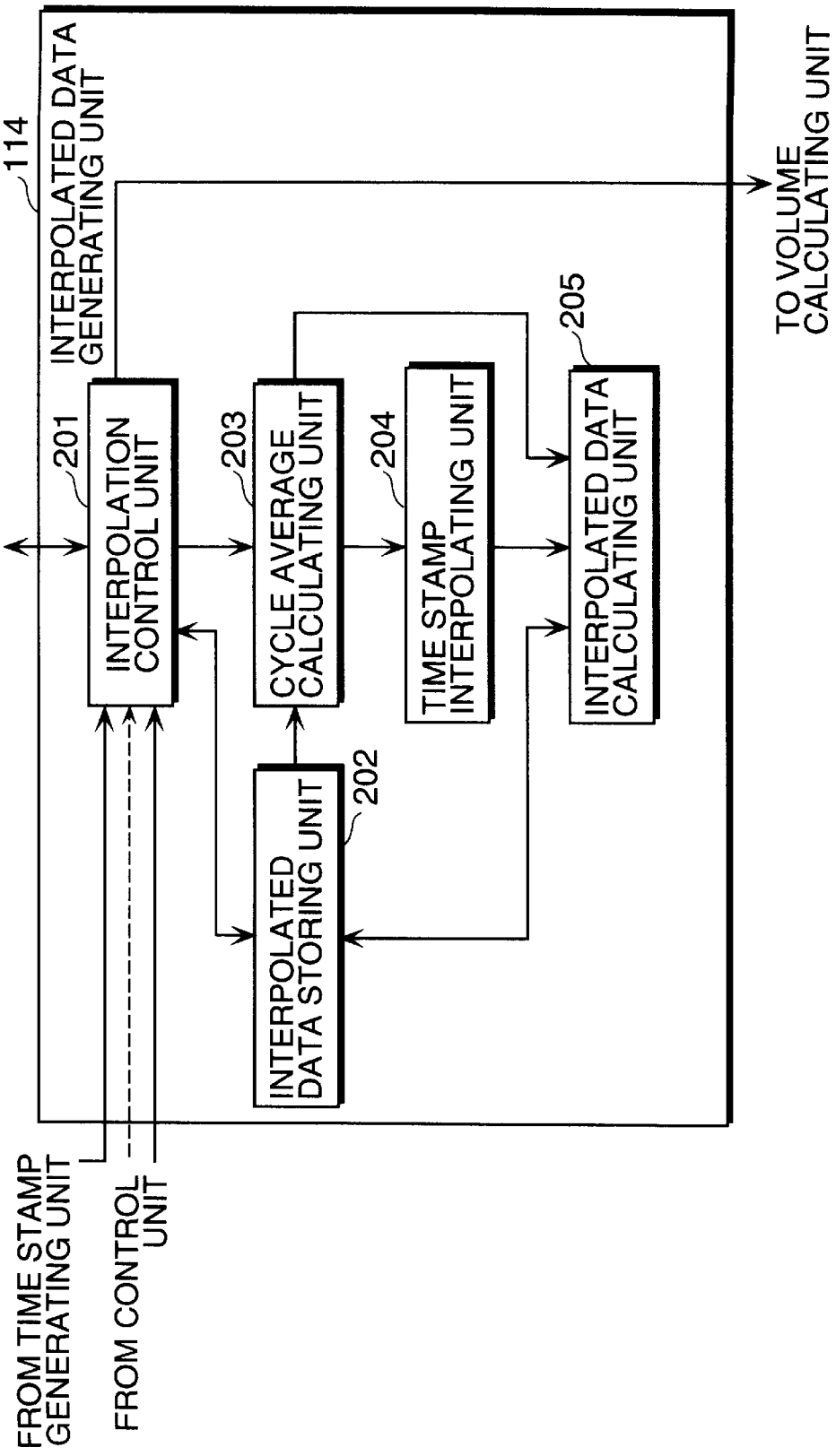
FIG. 6 is a block diagram showing a function configuration of an interpolated data generating unit of the ultrasonic diagnostic device.

FIG. 6 is a block diagram showing a detailed function configuration of the interpolated data generating unit 114 shown in FIG. 2. The interpolated data generating unit 114 includes an interpolation control unit 201, an interpolated data storing unit 202, a cycle average calculating unit 203, a time stamp interpolating unit 204, and an interpolated data calculating unit 205.

The interpolation control unit 201 controls transmission and reception of data used in the interpolated data generating unit 114. On receiving the parameters relating to the interpolation method and the pulsation cycle data from the control unit 116, the interpolation control unit 201 specifies the interpolation range, and obtains either image data or calculation data corresponding to the specified interpolation range from the data storing unit 112. The interpolation control unit 201 then places the obtained data and the received pulsation cycle data into the interpolated data storing unit 202.

After interpolation is completed, the interpolation control unit 201 sends interpolated image data or interpolated calculation data stored in the interpolated data storing unit 202 to the volume calculating unit 115.

The interpolated data storing unit 202 receives the pulsation cycle data and either the image data or the calculation data from the interpolation control unit 201, and stores them. The data storing unit 202 also stores the interpolated image data or the interpolated calculation data generated by the interpolated data calculating unit 205.

The cycle average calculating unit 203 obtains the pulsation cycle data from the interpolated data storing unit 202, and calculates an average of pulsation cycles included in the interpolation range.

The time stamp interpolating unit 204 normalizes values of time stamps attached to a plurality of sets of either image data or calculation data collected over a period corresponding to a plurality of pulsations. In other words, the time stamp interpolating unit 204 corrects time stamp values of the plurality of sets of image/calculation data in a manner that makes each pulsation cycle containing these time stamps equal to the average pulsation cycle calculated earlier. The time stamp interpolating unit 204 then sends the normalized time stamps to the interpolated data calculating unit 205.

The interpolated data calculating unit 205 receives the parameters relating to the interpolation method from the interpolation control unit 201, and also receives either image data or calculation data from the interpolated data storing unit 202. The interpolated data calculating unit 205 then performs interpolation on the received data. After interpolation, the interpolated data calculating 205 sends either the interpolated image data or the interpolated calculation data to the interpolated data storing unit 202.

Figure 7:
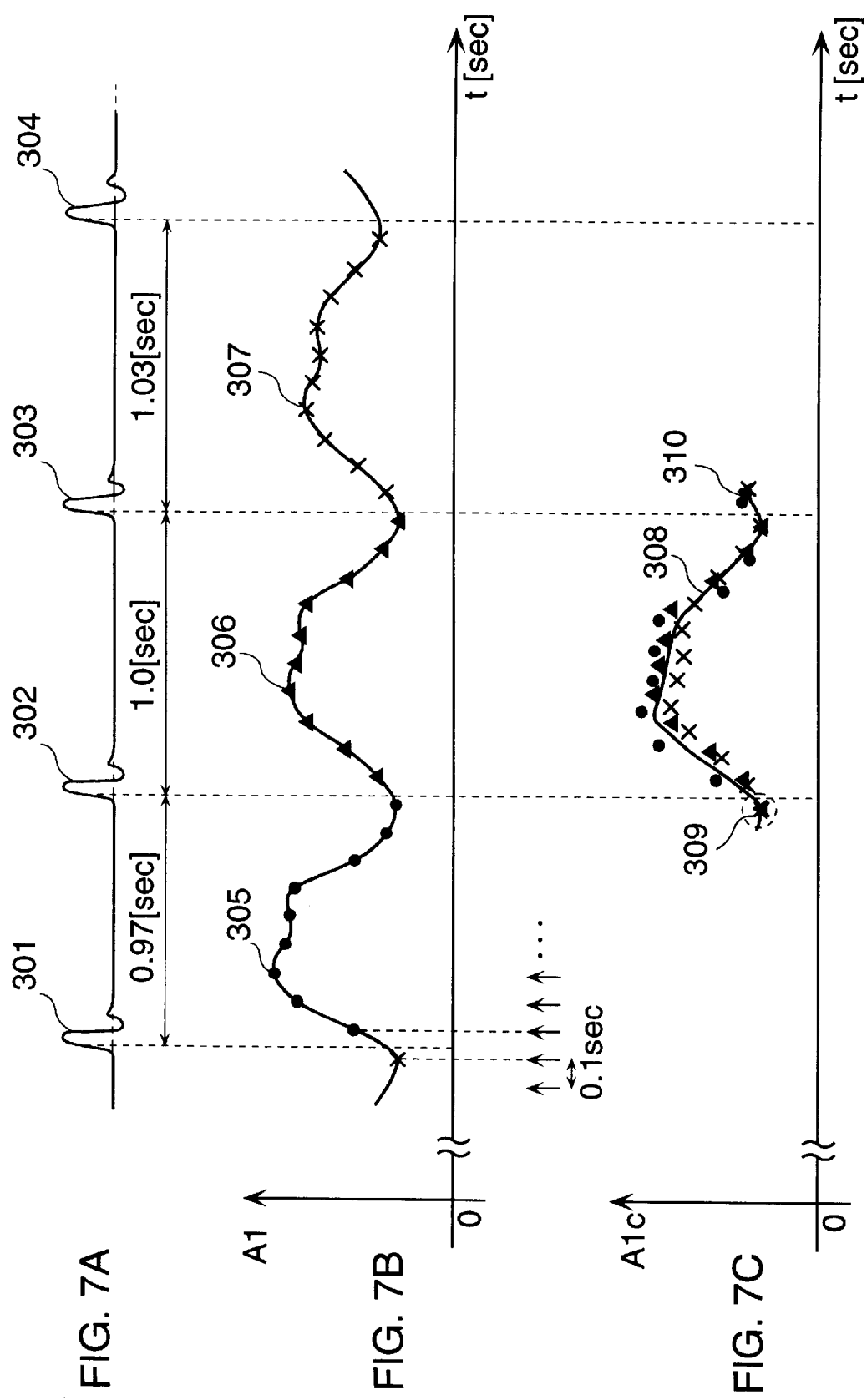
FIGS. 7A–7C are used to describe interpolation by the interpolated data generating unit.

FIGS. 7A–7C show representation of interpolation operation by the interpolated data generating unit 114 when it interpolates, for instance, between values of a radius "A1" (which is one of "Ai" out of "A1" to "A7") of a slice calculated based on a contour of a two-chamber image.

FIG. 7A shows three pulsation pulses 301–304 corresponding to an interpolation range containing three pulsation cycles designated by the operator. In this figure, an average of the pulsation cycles is 1.0 sec.

FIG. 7B shows measured values of the radius "A1" in the designated interpolation range. Sampled points in the first to third pulsation cycles 301–303 are represented by bullets, delta symbols, and crosses, respectively. For the example of this figure, sampling is performed at intervals of 0.1 sec.

FIG. 7C shows values of a post-interpolation radius "A1c" generated by interpolation based on the sampled values of the radius "A1" within the three pulsation cycles 305–307. A solid line in the figure represents the result of the interpolation, that is, change in values of the post-interpolation radius "A1c", with these values arranged at intervals of, for instance, 0.1 msec. The time stamp interpolating unit 204 normalizes a time axis for each pulsation cycle within the designated interpolation range in accordance with time stamp values. The interpolated data calculating unit 205 then superimposes values of the radius "A1" over one another within the same pulsation cycle for plotting, and generates an interpolation curve (such as that based on the B-spline) by using these plotted values.

To "normalize a time axis" means to calculate an average (1.0 sec., for this example) of the three pulsation cycles 305–307, and change time stamps with a premise that values of the radius "A1" change in accordance with the calculated average pulsation cycle. Plotting is then performed based on the same average pulsation cycle. This normalization therefore raises values of time stamps for the radius "A1" in the pulsation cycle 305, and lowers values of time stamps for the radius "A1" in the pulsation cycle 307.

The method for specifying the above interpolation curve by using the B-spline is as follows.

A B-spline "S(x)" with an order of "(K−1)" which passes N points (X0, Y0)~(XN−1, YN−1) is represented by an expression below.

$$S(X) = \Sigma a_i B_i, K(X) (i=0 \sim N-1)$$

By specifying the B-spline "S(X)", it becomes possible to calculate "Y" (the post-interpolation radius "A1c" for the present embodiment) for a given "X" (the time axis "t" for the present embodiment). The method of interpolation using such B-spline is described in detail in "C ni yoru Spline Kansu (Spline in C)", Keisuke Sugano et al., Tokyo Denki University Press, 1993.

The following describes the flow of operations for the ultrasonic diagnostic device 10 to calculate an LVV of the heart. The ultrasonic diagnostic device 10 accurately calculates an LVV in one of two operational modes consisting of real-time processing mode and non-real-time processing mode from which the operator selects. This operation can be roughly divided into the following two steps: a first half step for obtaining a two-chamber image; and a second half step for obtaining a four-chamber image after the operator turns the probe 13 for examination. The above "real-time processing" refers to an operation for examining change of the LVV in real time, and the "non-real-time processing" refers to an operation for more precisely examining change of the LVV after ultrasound images are processed.

Figure 8:
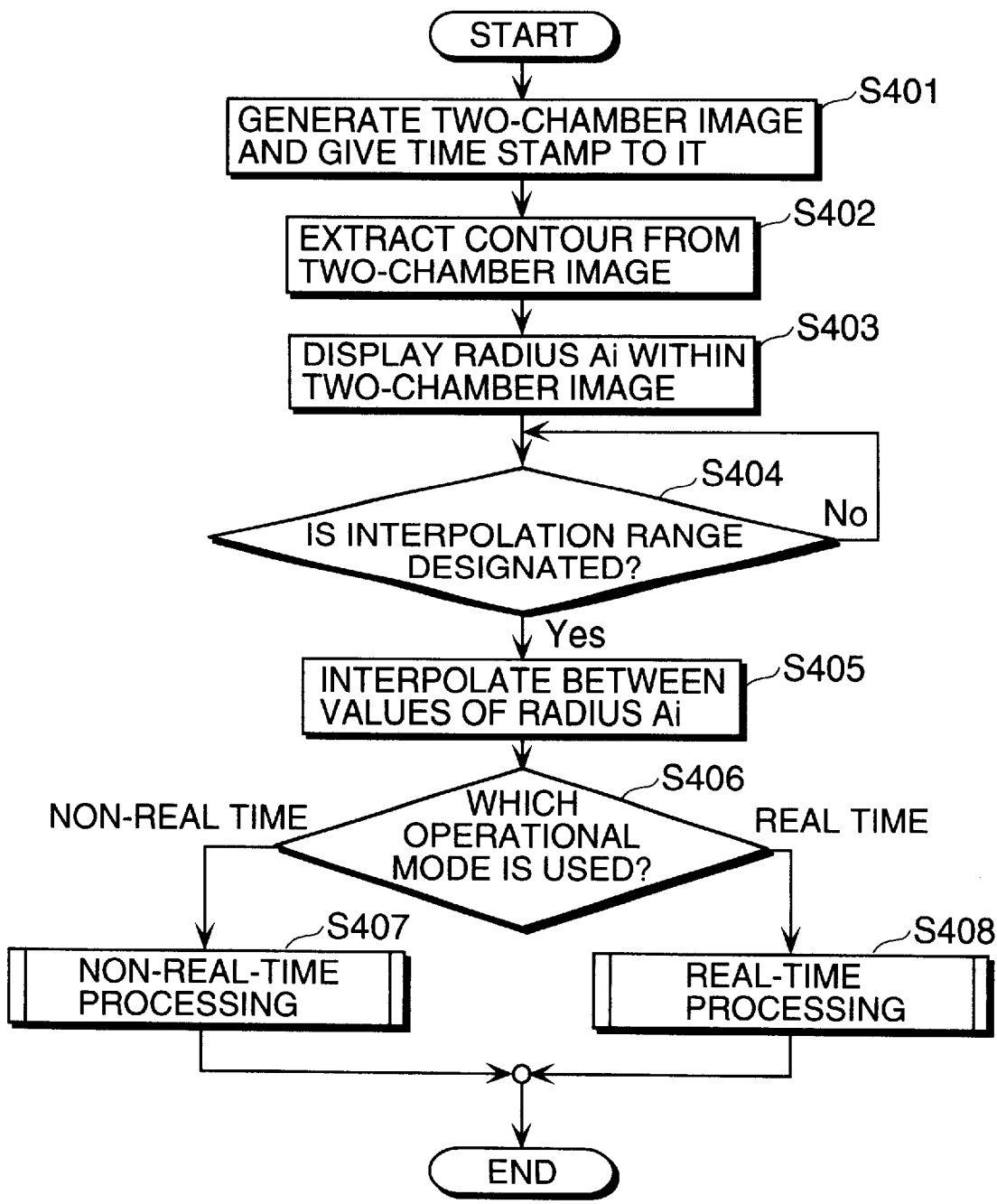
FIG. 8 is a flowchart showing processing for calculating a left ventricular volume (LVV) of a heart in real time and non-real time.

FIG. 8 is a flowchart showing the overall processing of the ultrasound diagnostic device 10 for calculating an LVV.

As the above first half step, the diagnostic device 10 performs steps S401–S405 as follows.

The image generating unit 110 receives an electric signal for image data of a two-chamber image around the LV through an operator's operation. Whenever it generates image data, the image generating unit 11 gives a time stamp to the image data, and sends it to the data storing unit 112 (step S401).

The contour extracting unit 113 obtains the image data from the data storing unit 112, extracts a contour of the LV from the obtained image data (step S402), and calculates the radius "Ai" (i=1~7, for instance) in the two-chamber image by using the extracted contour. This calculated radius "Ai" is later used in accordance with the Modified Simpson method. The contour extracting unit 113 then outputs the calculated radius "Ai" to the image displaying unit 106 (step S403).

After the above operations in steps S401–S403 have been repeated over a period corresponding to a plurality of pulsations, the operator designates an interpolation range for the radius "Ai" (step S404). Following this, the interpolated data generating unit 114 normalizes time stamps of values of the radius "Ai" within the designated interpolation range to superimpose these values on one another within the same pulsation cycle. The interpolated data generating unit 114 then interpolates between these values of the radius "Ai" to generate a data sequence of values of the radius "Ai" arranged at intervals of, for instance, 0.1 msec (step S405).

As the second half step, the ultrasonic diagnostic device 10 performs the processing from steps S406–S408 as follows. In accordance with the operational mode selected by the operator (step S406), the image processing unit 105 performs either the non-real-time processing (step S407) or the real-time processing (step S408).

Figure 9:
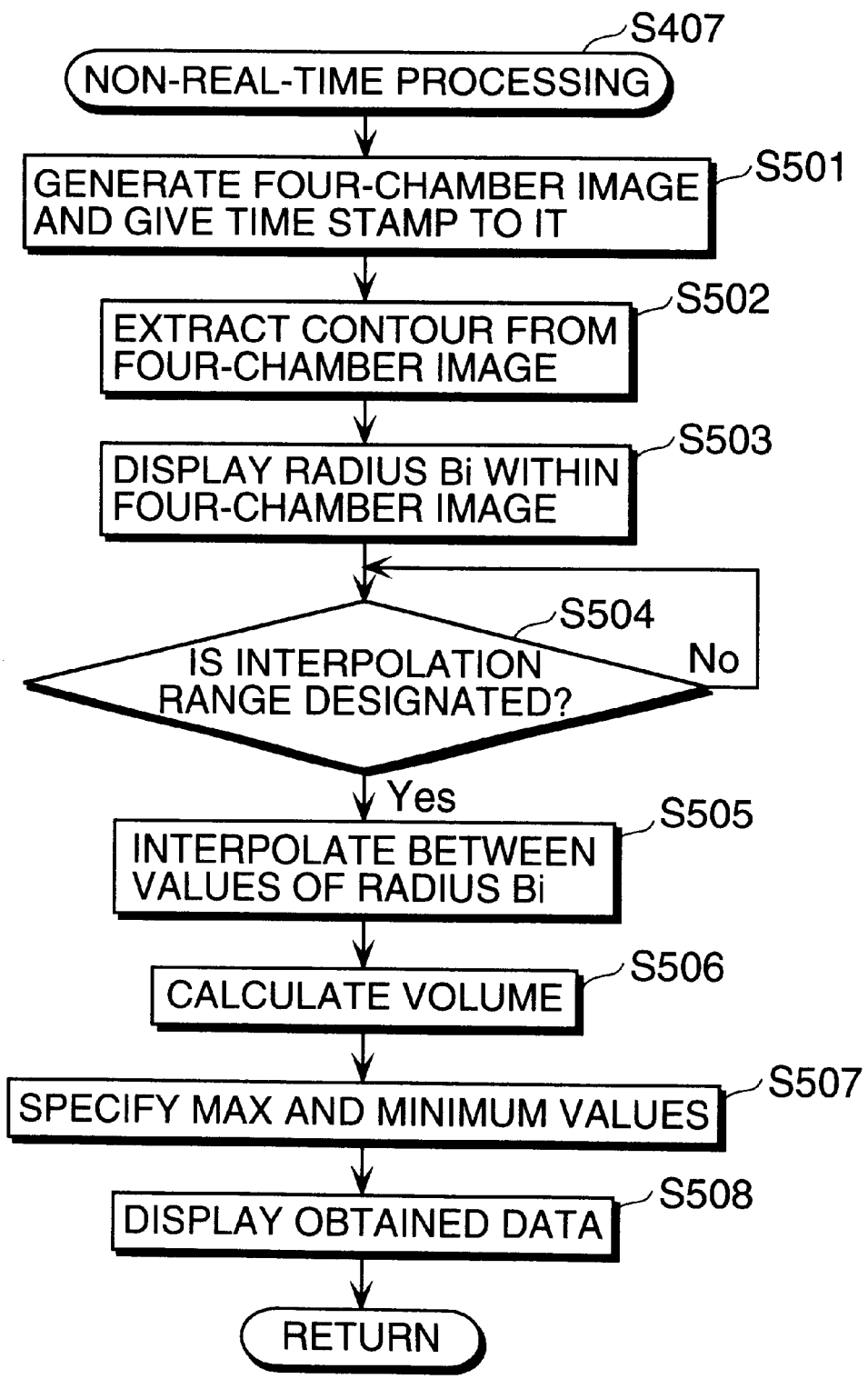
FIG. 9 is a flowchart showing processing to calculate an LVV of the heart in non-real time.

FIG. 9 is a flowchart showing the non-real-time processing in step S407 of FIG. 8 for calculating the volume "V" of the LV. The image generating unit 110 receives an electric signal for image data of a four-chamber image around the LV through an operator's operation. The image generating unit 11 then gives a time stamp to the image data, and sends the image data with the time stamp to the data storing unit 112 (step S501).

The contour extracting unit 113 obtains the four-chamber image data from the data storing unit 112, extracts a contour of the LV from the obtained four-chamber image data (step S502), and calculates a radius "Bi" (i=1~7, for instance) within the four-chamber image by using the extracted contour. The contour extracting unit 113 then outputs the radius "Bi" to the image displaying unit 106 (step S503).

After the above operations in steps S501–S503 have been repeated over a period corresponding to a plurality of pulsations, the operator designates an interpolation range for the radius "Bi" (step S504). The interpolated data generating unit 114 then normalizes time stamps of values of the radius "Bi" within the designated interpolation range, and superimposes these values on one another within the same pulsation cycle. The interpolated data generating unit 114 then interpolates between these values of the radiuses "Bi" to generate a data sequence of values of the radius "Bi" which are arranged at intervals of, for instance, 0.1 msec (step S505).

After this, the volume calculating unit 115 extracts a pair consisting of values of the radiuses "Ai" and "Bi" in the same phase from the data sequence of the radius "Bi" and that of the radius "Ai" generated earlier in the first half step, and substitutes the extracted values into the approximate expression in accordance with the Modified Simpson method to generate the volume "V" of the LV corresponding to one pulsation cycle. The volume calculating unit 115 repeats such calculation of the volume "V" within the pulsation cycle at intervals of, for instance, 0.1 msec (step S506), and specifies maximum and minimum values of the volume "V" within the pulsation cycle (step S507). The volume calculating unit 115 then outputs the maximum and minimum values, which are useful as an end-diastolic volume and an end-systolic volume, to the image displaying unit 106 (step S508).

Figure 10:
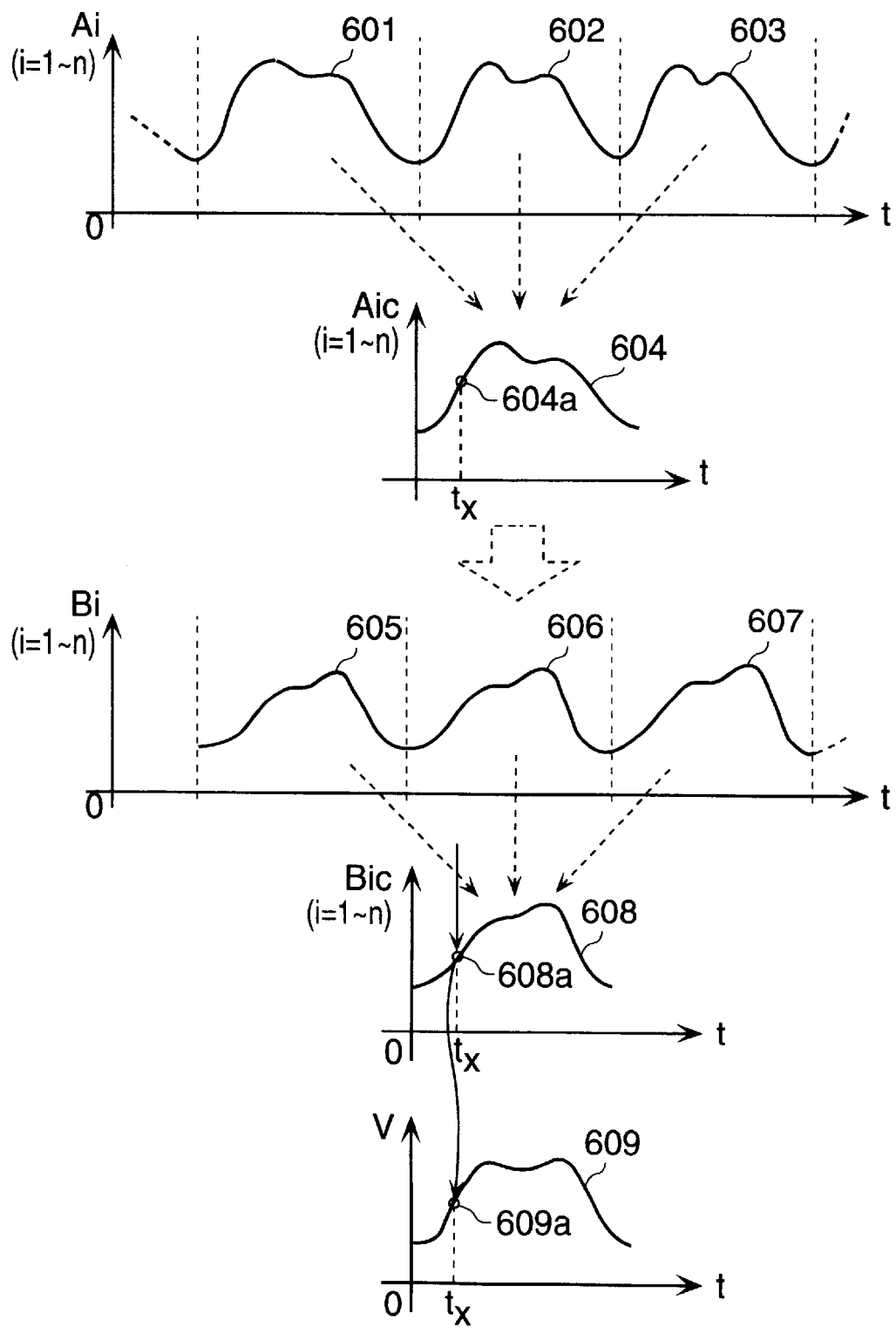
FIG. 10 shows representation of a process for calculating an LVV in non-real time.

FIG. 10 is used to explain the non-real-time processing shown in FIG. 9 for calculating the volume "V" of the LV. This figure shows a state in which a waveform 604 of values of a post-interpolation radius "Aic" (i=1~7, for instance) is calculated from three waveforms 601~603 for the radius "Ai" in the two-chamber image corresponding to an interpolation range designated by the operator. Also shown is a state in which a waveform 608 of values of a post-interpolation radius "Bic" (i=1~7, for instance) is calculated from three waveforms 605~607 for the radius "Bi" in the four chamber image corresponding to three pulsation cycles.

At the bottom of the figure is a waveform 609 for the volume "V" of the LV obtained from the waveforms 604 and 608 for the post-interpolation radiuses "Aic" and "Bic." A value 609a of the volume "V" corresponding to a time "tx", for instance, can be obtained from an expression below $$V=\Sigma AicBic \times hn \ (i=1\sim 7)$$

The post-interpolation radiuses "Aic" and "Bic" (i.e., values 604a and 608a) used in the above expression have the same time stamp that corresponds to the time "tx", that is, the same phase.

As has been described, with the above non-real-time processing, interpolation can be performed on calculation data obtained from two- and four-chamber images of the LV. More specifically, normalization relative to time is performed on sets of data corresponding to a plurality of pulsation cycles, and the normalized sets of data are superimposed over on another to specify an interpolation curve. Based on the specified interpolation curve, sets of data that were not sampled can be also specified. This generates data sequences containing sets of data that are arranged at shorter intervals. Following this, a pair of sets of data in the same phase is extracted from each data sequence to calculate volume and maximum and minimum values of the volume. Such processing eliminates noise and abnormal data and yields a volume value that is close to the actual volume, so that accurate diagnosis can be performed.

Figure 11:
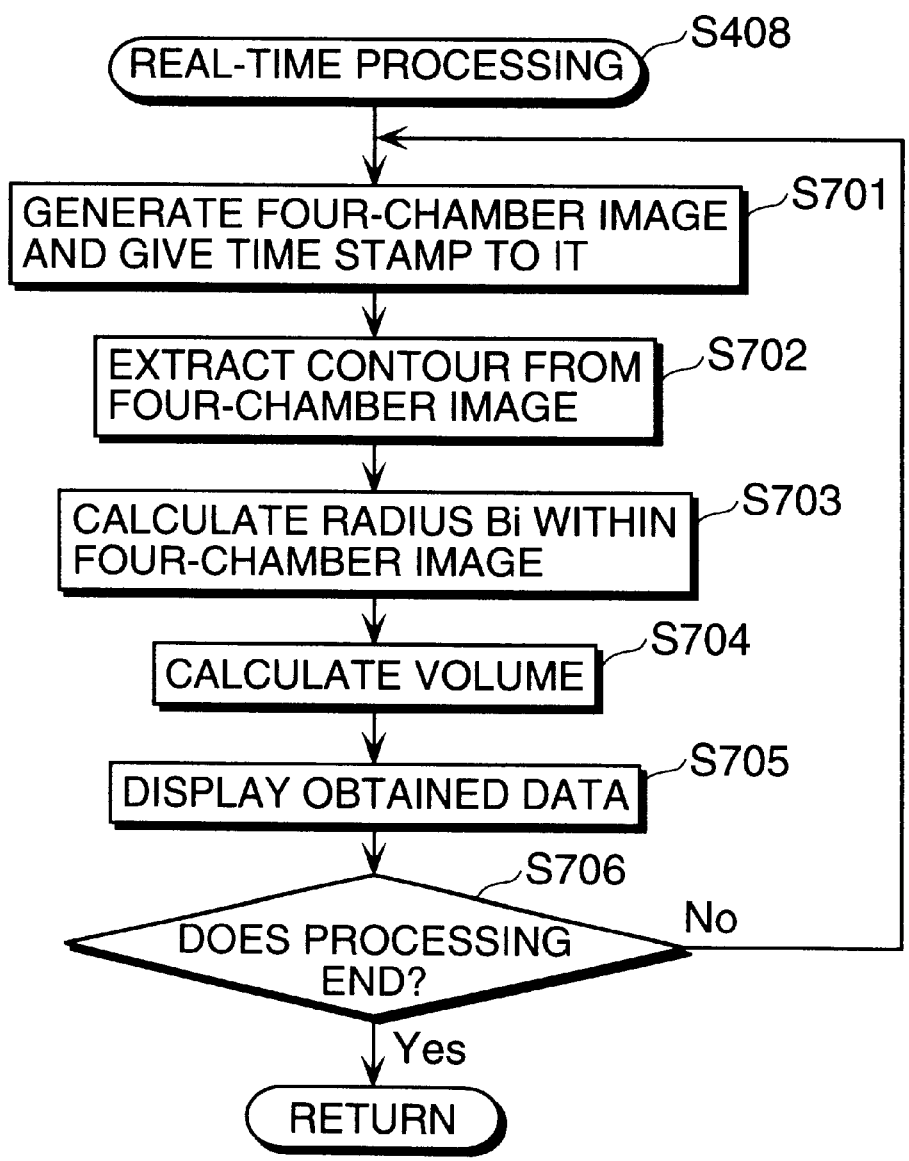
FIG. 11 is a flowchart showing processing to calculate an LVV in real time.

FIG. 11 is a flowchart showing the real-time processing in step S408 of FIG. 8 for calculating the volume "V" of the LV.

The image generating unit 110 receives an electric signal for image data, which corresponds to one frame, of a four-chamber image around the LV. The image generating unit 110 then gives a time stamp to the four-chamber image data, and sends them to the data storing unit 112 (step S701). The data storing unit 112 stores this four-chamber image data.

The contour extracting unit 113 obtains the four-chamber image data from the data storing unit 112, extracts a contour of the LV from the obtained four-chamber image data (step S702), and calculates a radius "Bi" from the extracted contour (step S703).

Following this, the interpolated data generating unit 114 normalizes a time stamp of the calculated radius "Bi" in accordance with a pulsation cycle that immediately precedes the current pulsation cycle. After this, the volume calculating unit 115 extracts a value of the radius "Ai" having the same time stamp as the above normalized time stamp from the sequence of values of the radius "Ai" generated earlier in the first half step. The volume calculating unit 115 then substitutes these values of the radiuses "Ai" and "Bi" in two- and four-chamber images in the same phase into the approximate expression in accordance with the Modified Simpson method to calculate the volume "V" of the LV (step S704). The volume calculating unit 115 then outputs the calculated volume "V" to the image displaying unit 106 (step S705).

The above operations in steps S701–S705 are repeated whenever an electric signal for image data corresponding to one frame is outputted to the image processing unit 115 (step S706).

Figure 12:
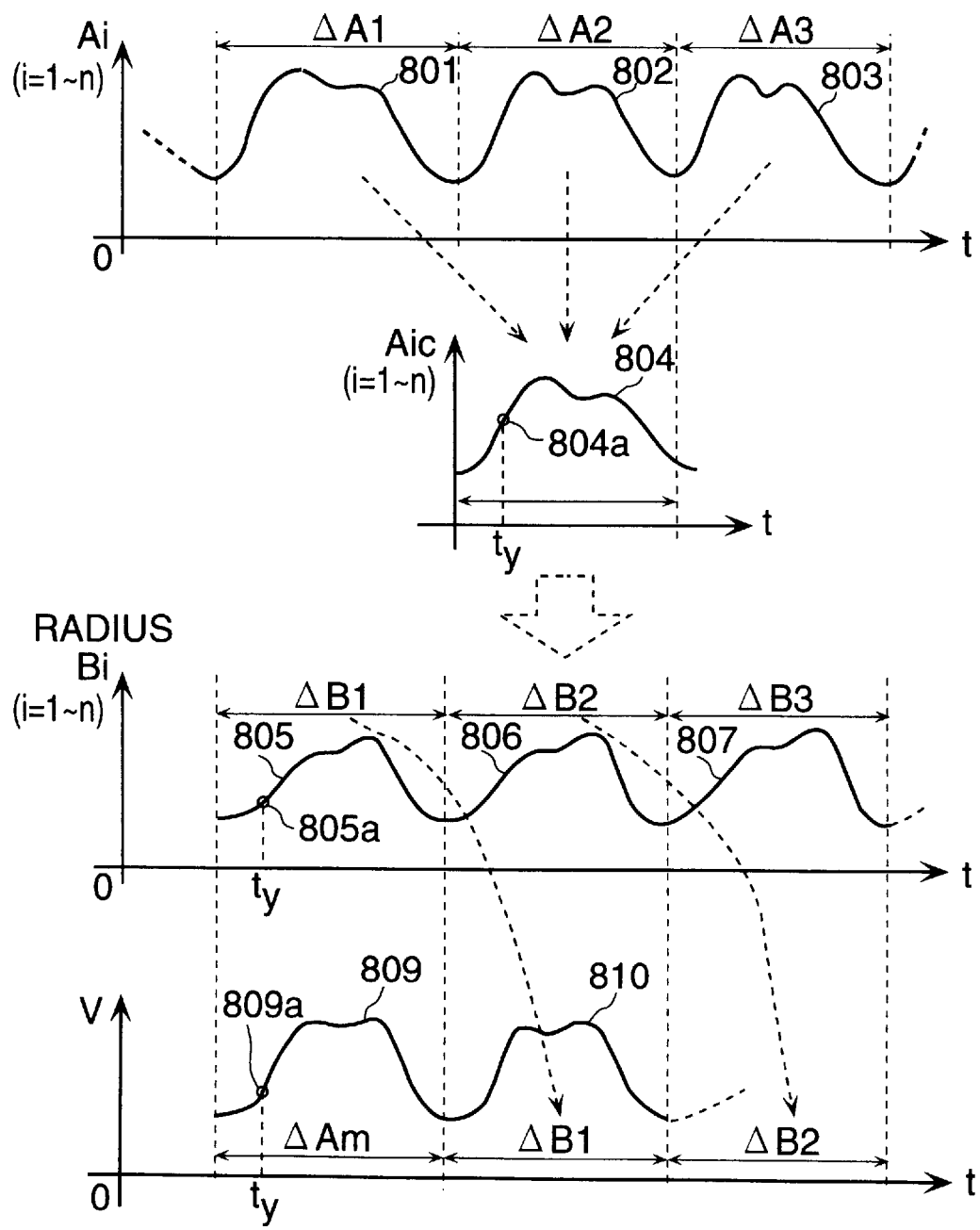
FIG. 12 shows representation of a process for calculating an LVV in real time.

FIG. 12 is used to explain the above real-time processing shown in FIG. 11 for calculating the volume "V" of the LV in real time. As in the stated non-real-time processing, a waveform 804 of values of a post-interpolation radius "Aic" (i=1~7) is calculated from waveforms 801–803 of values of the radius "Ai" within three pulsation cycles in the first half step.

In the second half step, however, the measured value of the radius "Bi" (i=1~7) in the four-chamber image is used as it is for calculating the volume "V." This is because it is impossible to superimpose waveforms corresponding to a plurality of pulsation cycles over one another to perform interpolation on these waveforms.

In more detail, whenever the four-chamber image data corresponding to one frame is generated, the volume calculating unit 115 calculates a value 809a of the volume "V" from a value 805a of the radius "Bi" in the four-chamber image data and from a value 804a of the post-interpolation radius "Aic" that has a same time stamp "ty" as a normalized time stamp "ty" given to the value 805a of the radius "Bi." When this processing is repeated at a certain frame rate, waveforms 805–807 for the four-chamber image data can be obtained in parallel to waveforms 809–810 for the volume "V."

Note that a time stamp of a value of the above radius "Bi" within the four-chamber image is normalized on the presumption that a pulsation cycle containing the time stamp to be normalized is made equal to an immediately preceding pulsation cycle. For instance, a first pulsation cycle ΔB1 shown in FIG. 12 is presumed to become equal to an average pulsation cycle ΔAm in which the post-interpolation radius "Aic" in the two-chamber image data has been obtained. On such presumption, each time stamp of the radius "Bi" is normalized in accordance with the pulsation cycle ΔAm. Similarly, a second pulsation cycle ΔB2 is presumed to become equal to the immediately preceding first pulsation cycle ΔB1, and each time stamp of the radius "Bi" within the second pulsation cycle ΔB2 is normalized in accordance with the first pulsation cycle ΔB1.

By performing the above real-time processing, the ultrasonic diagnostic device 10 calculates an LVV of the heart from interpolated two-chamber image data and measured four-chamber image data, and displays change in the calculated volume at a certain frame rate. This instantaneously provides change in the LVV to the operator, who can therefore quickly perform examination under different examination conditions such as by turning the probe 13.

Figure 13:
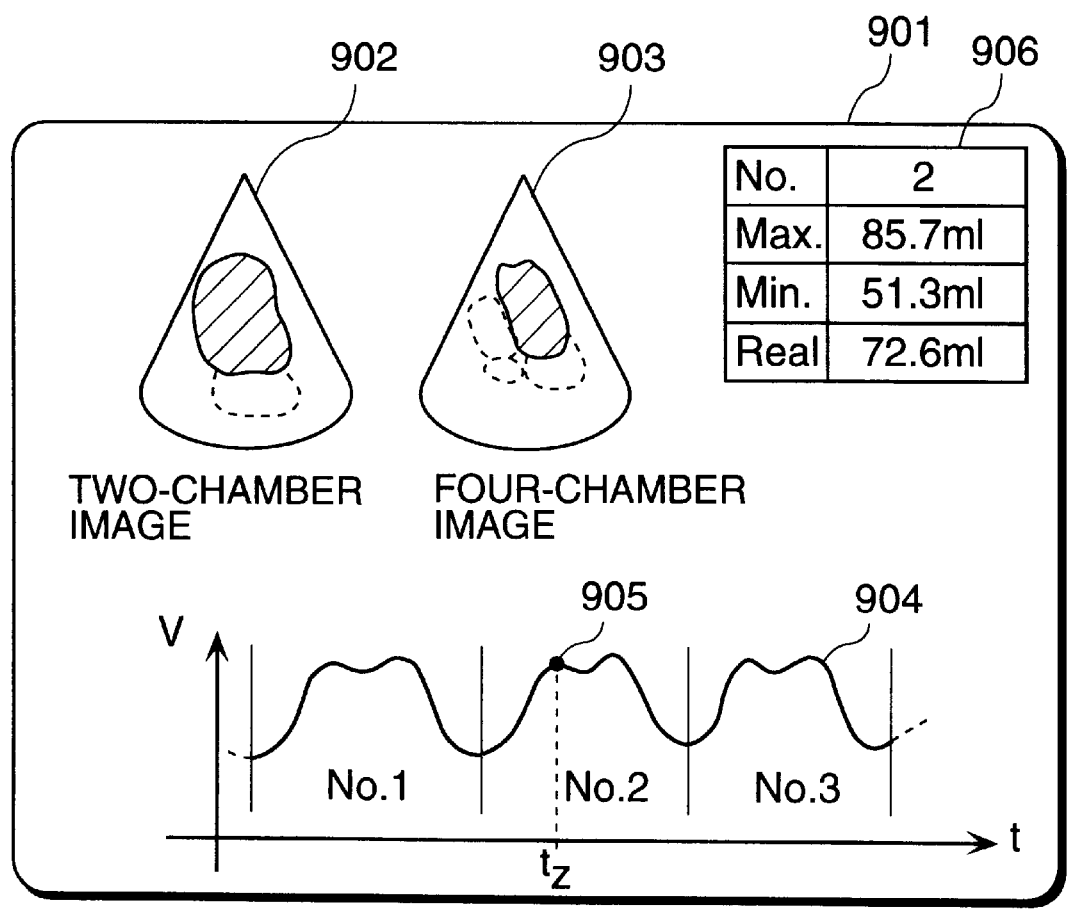
FIG. 13 shows an example screen containing an LVV which is obtained by interpolation.

FIG. 13 shows an example screen displayed by the image displaying unit 106 when the non-real-time processing shown in FIGS. 8–10 is performed. Displayed in the lower part of the screen is a curve representing change in the volume "V" of the LV in three pulsation cycles. Displayed in the upper right corner of the screen is diagnostic information for a time "tz" which the operator designates by placing a cursor 905 on it. This diagnostic information includes the following: a pulsation number given to a pulsation cycle in which the cursor 905 is placed; a maximum value "Max." and a minimum value "Min." of the volume "V" in this pulsation cycle; and a value "Real" of the volume "V" at the time "tz." At higher left are two- and four-chamber views of the heart at the time "tz." With such variety of diagnostic information, the operator can accurately examine an object of interest from different perspectives.

As has been described, the present ultrasonic diagnostic device 10 obtains the radius "Ai" in a two-chamber image and the radius "Bi" in a four-chamber image from contours of these images that have been sampled. The diagnostic device 10 then interpolates between values of the radiuses "Ai" and "Bi" in accordance with a time stamp that is reset each time the pulsation detecting unit 103 detects a pulsation. Consequently, data sequences containing sets of data arranged at shorter intervals can be generated. This can provide the radiuses "Ai" and "Bi" in the same phase even when phases for measured radiuses "Ai" and "Bi" are different, so that accurate calculation can be performed using the radiuses "Ai" and "Bi."

Although the ultrasonic diagnostic device of the present invention has been described by using the above embodiments, it should be clear that the present invention is not limited to the above embodiments.

For instance, interpolation may be performed on image data (i.e., 2D density data), or on a cross-sectional area of an object subject to examination indicated by a contour of a two-chamber image or a four-chamber image although the above embodiment describes, as one example, interpolation on the radiuses "Ai" and "Bi" within the two- and four-chamber images.

Figure 14:
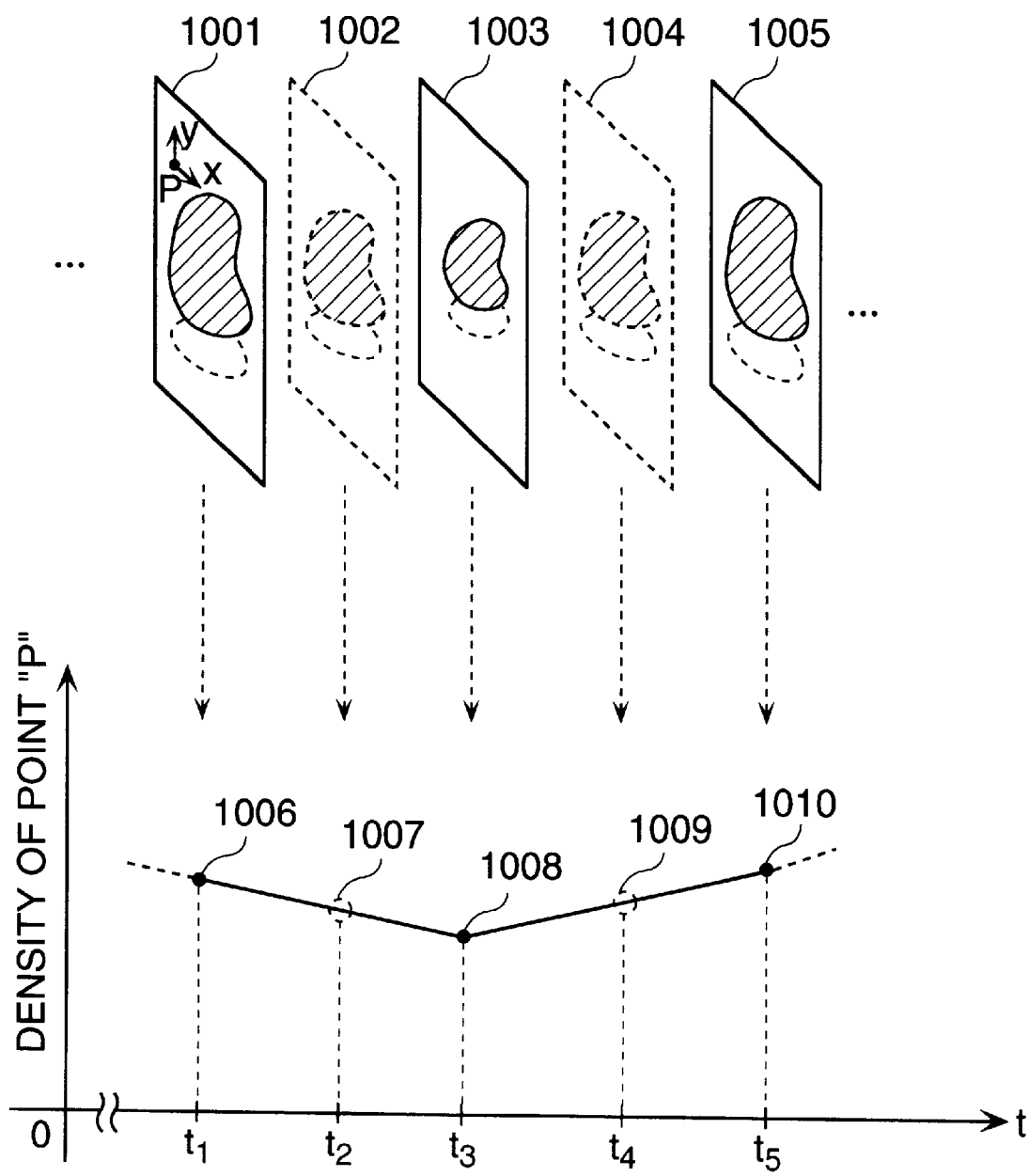
FIG. 14 is used to describe relationship between sampled image data and interpolated image data when interpolation is performed on image data.

FIG. 14 shows relationship between sampled image data and interpolated image data when interpolation is performed on image data. In the figure, density of a point P(X, Y) within a frame is focused on, and linear interpolation is performed between image data 1001, 1003, and 1005 generated by sampling so that new image data 1002 and 1004 is generated.

In more detail, linear interpolation is performed between measured density values 1006, 1008, and 1010 of the point P(X, Y) at sampled times "t1", "t3", and "t5" so that new density values 1007 and 1009 corresponding to sampled times "t2" and "t4" are generated. When interpolation is performed on image data in this way, image data corresponding to 30 fps can be generated from image data generated by sampling at a frame rate of, for instance, 10 fps. This achieves more precise ultrasonic examination.

Figure 15:
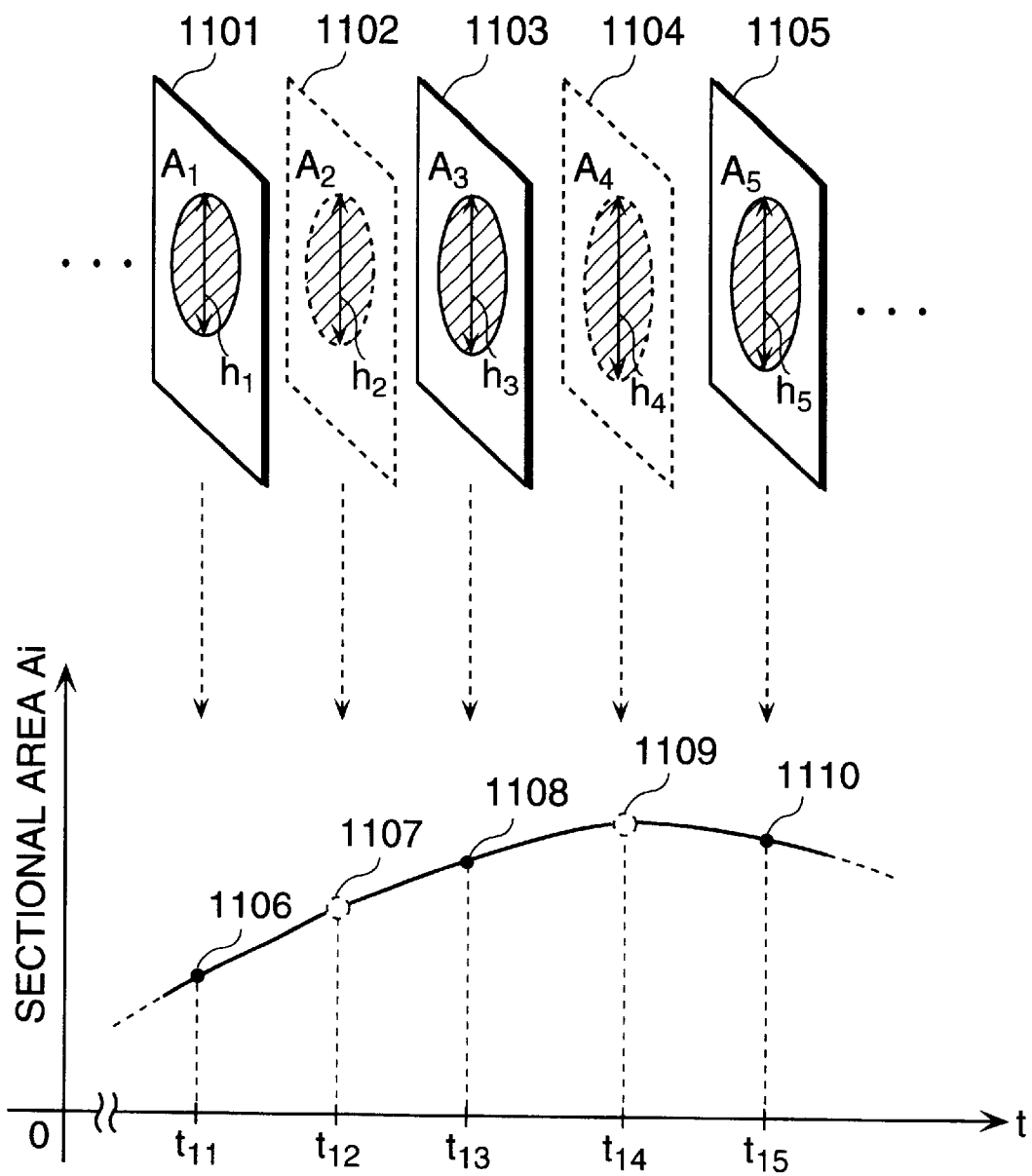
FIG. 15 is used to describer relationship between a cross-sectional area based on sampled data and a cross-sectional area obtained through interpolation when the interpolation is performed on cross-sectional area to calculate an LVV.

FIG. 15 shows a case in which interpolation is performed on cross-sectional areas of an object to be examined so as to calculate the object's volume. Relationship between cross-sectional areas based on sampled data and cross-sectional areas generated by interpolation is also shown. Here, a cross-sectional area of the object within an ultrasound image of a frame is focused on to be interpolated.

More specifically, interpolation is performed between values 1106, 1108, and 1110 of a cross sectional area "Ai" which are calculated from objects within ultrasound images (contour data 1101, 1103, and 1105 at sampled times "t11", "t13", and "t15) generated by sampling. This interpolation generates values 1107 and 1109 of the cross-sectional area "Ai" corresponding to sampled times of "t12" and "t14." The cross-sectional area "Ai" can be specified by measuring a total number of pixels surrounded by a contour, and is used in an approximate expression according to the Simpson method or the single plane area length method to specify the object's volume.

In this way, change in the object's volume can be easily and quickly obtained by interpolating between values of a cross-sectional area of a contour obtained from image data corresponding to a single cross section.

For the above embodiment, three sets of calculation data corresponding to three consecutive pulsation cycles are extracted to be superimposed on one another. However, it is alternatively possible to extract six sets of calculation data corresponding to six consecutive pulsation cycles, separate the extracted six sets into three two-sets of calculation data, and superimpose respective two sets of calculation data over one another. Alternatively, two consecutive sets of data may be extracted and superimposed over each other. This can achieve interpolation (i.e., function fitting) targeting a wider range, including both crests and troughs of a waveform representing change in calculation data and near the waveform, so that accurate maximum and minimum values can be obtained.

For the above embodiment, the interpolation range is designated by the operator. However, it is also possible to provide a default of the interpolation range to allow, for instance, consecutive three pulsation cycles to be automatically selected as an interpolation range for either two- and four-chamber images or calculation data.

The processing characteristic of the image processing unit 105 of the present ultrasonic diagnostic device 10 may be applied to not only an ultrasound image generated by the diagnostic device 10 but also ordinary images generated by devices such as a digital video camera. By embodying such processing of the image processing unit 105 as a program and having a computer such as a personal computer execute this program, a general-purpose image processing device with interpolation function according to the present invention can be achieved.

Second Embodiment

The first embodiment describes the ultrasonic diagnostic device 10 capable of precisely calculating volume of an object such as an LV of a heart by interpolating between image data or calculation data based on sampled ultrasonic image data so as to increase an apparent sampling rate of the interpolated data. The second embodiment describes an ultrasonic diagnostic device capable of more precisely calculating volume of an object by predicting an end-systolic time and an end-diastolic time and by obtaining an electric signal at the predicted times.

The following describes the ultrasonic diagnostic device 30 of the second embodiment with reference to drawings.

Figure 16:
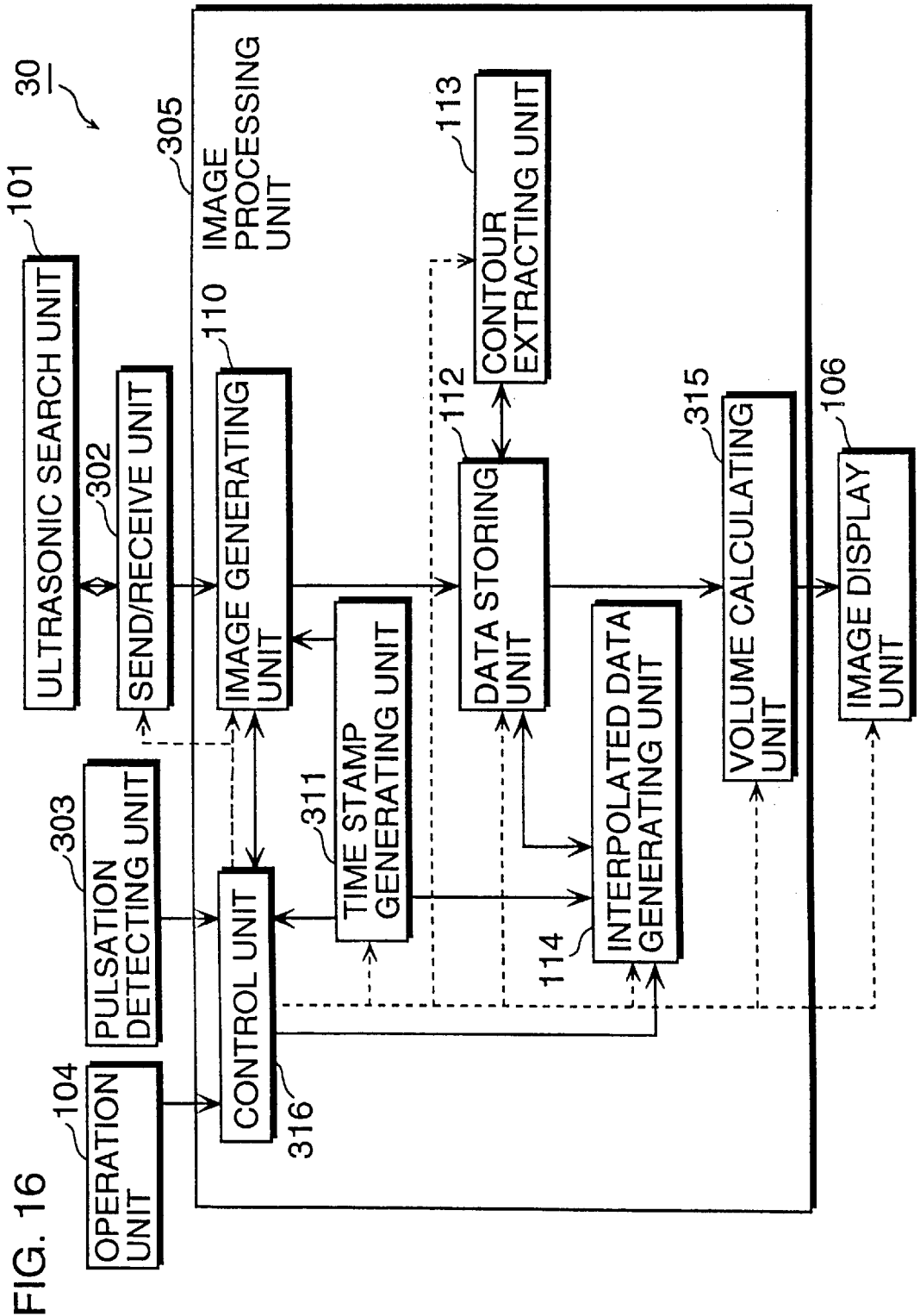
FIG. 16 is a block diagram showing a main function configuration of an ultrasonic diagnostic device according to the second embodiment of the invention.

FIG. 16 is a block diagram showing a function configuration of the ultrasonic diagnostic device 30. In accordance with ultrasound images and a sampled action potential signal (hereafter called an ECG (electrocardiogram) signal), the present diagnostic device 30 not only calculates an LVV of a heart but also predicts end-systolic and end-diastolic times and obtains an electric signal at the predicted times. The diagnostic device 30 includes the following main elements: an ultrasonic search unit 101, a send/receive unit 302, a pulsation detecting unit 303, an operation unit 104, an image processing unit 305, and an image display unit 106. The image processing unit 305 contains an image generating unit 110, a time stamp generating unit 311, a data storing unit 112, a contour extracting unit 113, an interpolated data generating unit 114, a volume calculating unit 315, and a control unit 316.

Out of the above elements, the same elements as in the first embodiment are given reference numbers used in the first embodiment and will not be described. The following description focuses on elements characteristic of the present ultrasonic diagnostic device 30.

The send/receive unit 302 has the same function as the unit 102 of the first embodiment. In addition to this function, the send/receive unit 302 has a sender/beam former generate ultrasound and has a receiver/beam former receive an ultrasound echo in accordance with an instruction from the control unit 316.

The pulsation detecting unit 303 has the same function as the unit 103 of the first embodiment. In addition to this function, the detecting unit 303 includes an ECG electrode (not shown in the figure) for obtaining the ECG signal and sends the obtained ECG signal to the control unit 316.

The image processing unit 305 includes a time stamp generating unit 311, a volume calculating unit 315, and a control unit 316, instead of the units 111, 115, and 116, respectively, of the first embodiment.

The time stamp generating unit 311 has the same function as the unit 111 of the first embodiment. In addition to this function, the time stamp generating unit 311 receives an instruction from the control unit 316, and sends a time stamp value corresponding to a time of reception of the instruction to the control unit 316.

The volume calculating unit 315 has the same function as the unit 115 of the first embodiment. Other than this function, the calculating unit 315 sends a calculated volume value of the LV to the control unit 316 in every pulsation cycle.

The control unit 316 has the same function as the unit 116 of the first embodiment. In addition to this function, the control unit 316 has an end-time prediction function. With this prediction function, the control unit 316 predicts an end-diastolic time and an end-systolic time at which an LVV becomes a local maximum and a local minimum, respectively, and gives an instruction to the send/receive unit 302 to obtain an electric signal at the predicted end-diastolic and end-systolic times.

More specifically, the control unit 316 receives the ECG signal from the pulsation detecting unit 303, and at the same time performs A/D conversion on the received ECG signal to generate digital values. The control unit 316 stores the generated digital values, and detects, in each pulsation cycle, a negative-maximum state in which a value of the ECG signal becomes a negative maximum (or local maximum) in the pulsation cycle and a zero-cross state in which a value of the ECG signal value becomes zero.

The control unit 316 detects the negative-maximum state as follows. The control unit 316 compares every two consecutively obtained values of the ECG signal after the A/D conversion with each other to find a difference of the two values. When a sign of the obtained difference is plus (i.e., a slope of the ECG waveform is positive), the control unit 316 instructs the time stamp generating unit 311 to send a time stamp that corresponds to a value which has been obtained earlier than the other value out of the two compared values, associates the sent time stamp with the value, and stores them. At the end of each pulsation cycle, the control unit 316 specifies a negative maximum value out of the stored values, so that a negative-maximum state in each pulsation cycle is detected. Following this, the control unit 316 specifies a time (hereafter called "a negative-maximum time") corresponding to the specified negative maximum value by referring to a time stamp associated with the specified negative maximum value. As the zero-cross state, the control unit 316 detects a state in which a sign of a digital value of the ECG signal changes. In each pulsation cycle, the control unit 316 detects two zero-cross states: (a) a first zero-cross state in which a value of the ECG signal changes from the negative maximum value to zero; and (b) a second zero-cross state in which a value of the ECG signal changes from a plus value to zero. After detecting the first and second zero-cross states, the control unit 316 specifies times corresponding to the two detected zero-cross states by referring to time stamps corresponding to the detected two zero-cross states.

Following this, the control unit 316 regards the specified times for the first and second zero-cross states as end-diastolic and end-systolic times, respectively. The above A/D conversion on a value of the ECG signal is performed, for instance, with a sampling frequency of 10 KHz and a resolution of 32 bits.

FIGS. 17A–17D are used to explain the end-time prediction function of this control unit 316. FIG. 17A shows a waveform of a pulsation pulse, and FIG. 17B shows a waveform of the ECG signal. FIG. 17C shows changes in the volume "V" of the LV, and FIG. 17D shows a representation of a time stamp whose value increases monotonously. As is known, times (i.e., "D1"–"D3" and "S1"–"S3" for this figure) at which the ECG signal becomes zero correspond to end-diastolic times (i.e., "D1"–"D3") and end-systolic times (i.e., "S1"–"S3").

As shown in FIGS. 17A and 17B, a time stamp 1741 is incremented beginning at a time "T0" when a first pulsation 1700 is detected.

While performing A/D conversion on the ECG signal, the control unit 316 specifies the negative-maximum time, the end-diastolic time, and the end-systolic time in each pulsation cycle by using values of time stamps sent from the time stamp generating unit 311.

The control unit 316 performs the above series of operations over three pulsation cycles 1725–1727 so that end-diastolic times "D1"–"D3" and end-systolic times S1–S3 in these pulsation cycles 11725–1727 are specified.

The control unit 316 then calculates an average of a period between the times "D1"–"D2" and a period between the times "D2"–"D3", and adds the calculated average value to the time "D3" to predict an end-diastolic time "D4" for a next pulsation cycle 1728. Similarly, the control unit 316 predicts an end-systolic time "S4" in the pulsation cycle 1728 from a period between the end-systolic times "S1" and "S2" and a period between the end-systolic times "S2" and "S3."

Similarly, the control unit 316 predicts an end-diastolic time "D5" and an end-systolic time "S5" (not shown in the figure) in a pulsation cycle 1729 (also not shown in the figure) from measured values in the pulsation cycles 1726–1728. In this way, the control unit 316 conducts prediction in every pulsation cycle. Here, the control unit 316 may calculate a difference between an predicted value and a measured value to correct the predicted value in accordance with the calculated difference.

The following describes the processing of the above ultrasonic diagnostic device 30 with reference to FIGS. 17A–17D and FIG. 18.

Figure 18:
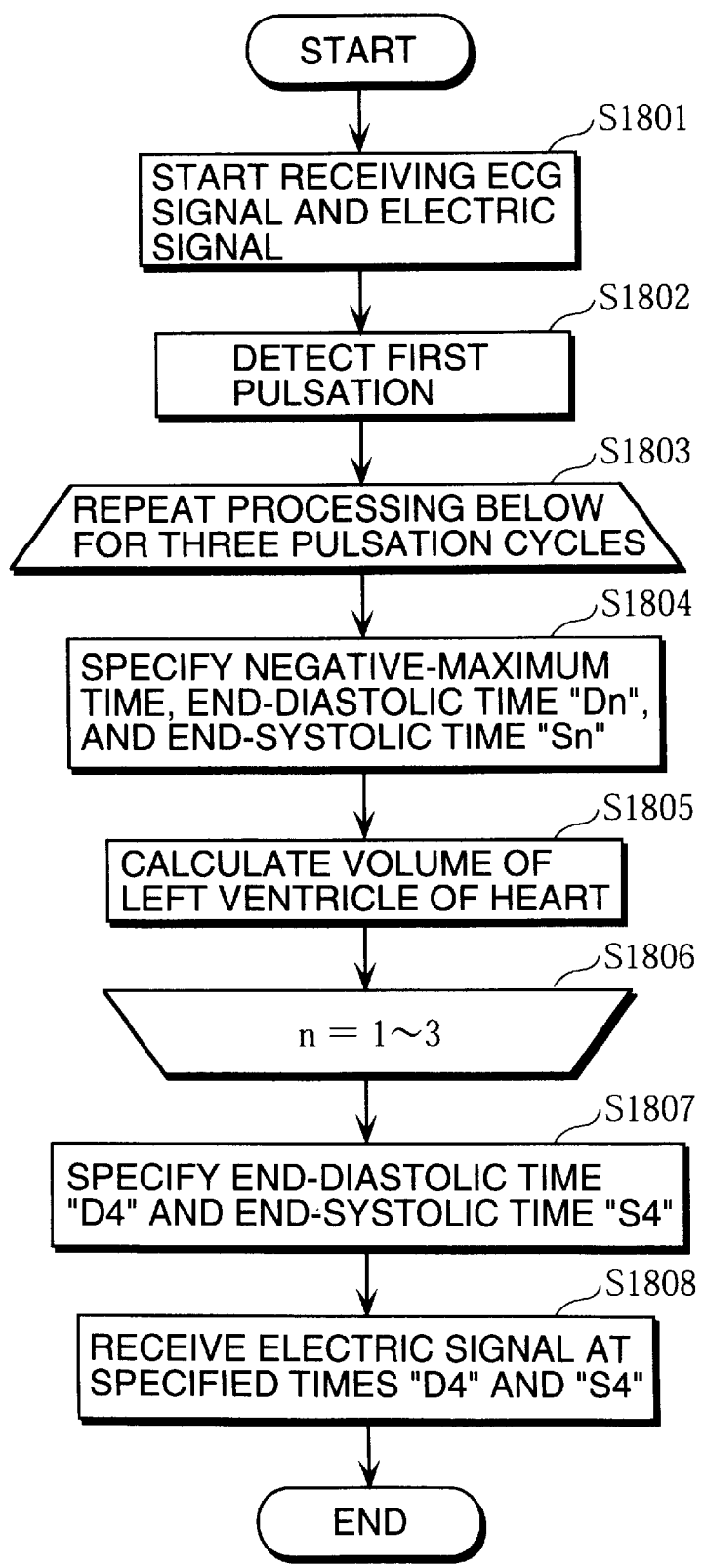
FIG. 18 is a flowchart showing the processing of the end-time prediction function by the above control unit.

FIG. 18 is a flowchart showing the processing of the end-time prediction function by the control unit 316.

As soon as the control unit 316 receives an ECG signal and an ultrasound image starts to be generated (step S1801), the control unit 316 detects a first pulse pulsation (step S1802).

While performing A/D conversion on the received ECG signal, the control unit 316 specifies a negative-maximum time, an end-diastolic time "Dn", and an end-systolic time "Sn" (step S1804). The control unit 316 also calculates an LVV and its maximum and minimum values in a pulsation cycle as in the first embodiment (step S1805).

The control unit 316 repeats the above processing over three pulsation cycles 1725–1727 (steps S1803–S1806).

After this, the control unit predicts the end-diastolic time "D4" and the end-systolic time "S4" in the next pulsation cycle 1728 from the specified end-diastolic times "D1–D3" and end-systolic times "S1–S3" in the pulsation cycles 1725–1727 (step S1807).

Finally, the control unit 316 instructs the send/receive unit 302 to obtain an electric signal at the predicted end-diastolic time "D4" and end-systolic time "S4" (step S1808), so that the send/receive unit 302 has ultrasound transmitted and receives an ultrasonic echo, and the image generating unit 110 generates an ultrasound image from the received ultrasonic echo.

As has been described, the present ultrasonic diagnostic device 30 is capable of predicting an end-diastolic time and an end-systolic time of the LV of the heart, and obtaining an electric signal at the predicted times. Consequently, the present diagnostic device 30 can more accurately calculate maximum and minimum values of the LVV.

For the above embodiment, an end-diastolic time "D4" is predicted by calculating an average of the period between the times "D1"–"D2" and the period between the times "D2"–"D3" and by adding the calculated average to the time "D3." However, it is alternatively possible to predict the end-diastolic time "D4" by simply adding the period between the times "D2"–"D3" to the time "D3." A number of pulsation cycles used for the end-time prediction is not limited to three or two, and may be a given number. The end-time prediction method is also not limited to the above method using the above difference, and may use a disclosed ordinary mathematical method, such as interpolation based on an n-order function or a spline curve.

It is alternatively possible to specify times at which the LVV becomes maximum and minimum values by using time stamps corresponding to these values, predict end-diastolic and end-systolic times from the specified times, and obtain an electric signal at the predicted end-diastolic and end-systolic times.

What is claimed is:

1. An ultrasonic diagnostic device operable to generate and display an ultrasound image containing an image of a subject-object in accordance with reflection of ultrasound, said ultrasonic diagnostic device comprising:

an image generating unit operable to successively generate a plurality of ultrasonic images, wherein each ultrasonic image includes a contour of a cross section of the subject-object;

a quantity extracting unit operable to extract, for each respective ultrasonic image, a respective cross-sectional dimension value based on the contour included in the respective ultrasonic image;

a time stamp generating unit operable to generate, for each respective ultrasonic image, a respective time stamp indicating a time at which the respective ultrasonic image was generated, and to associate the respective time stamp with the respective cross-sectional dimension value as a respective data pair;

an interpolating unit operable to perform interpolation on at least two of the extracted cross-sectional dimension values so as to generate an interpolated cross-sectional dimension value corresponding to a time other than the times indicated by the time stamps contained in the data pairs that contain the at least two extracted cross-sectional dimension values, respectively;

an information generating unit operable to generate diagnostic information related to the whole subject-object in accordance with the extracted cross-sectional dimension values and the interpolated cross-sectional dimension value; and a display unit operable to display the generated diagnostic information.

2. The ultrasonic diagnostic device of claim 1, wherein said interpolating unit is operable to perform the interpolation a plurality of times so as to generate a respective plurality of interpolated cross-sectional dimension values, and said information generating unit is operable to generate the diagnostic information related to the whole subject-object in accordance with the extracted cross-sectional dimension values and the plurality of interpolated cross-sectional dimension values.

3. The ultrasonic diagnostic device of claim 2, further comprising:

a pulsation detecting unit operable to detect every pulsation related to the subject-object; and a clock unit operable to measure an elapsed time from the detection of each pulsation;

wherein the time indicated by each time stamp is an elapsed time measured by said clock unit.

4. The ultrasonic diagnostic device of claim 3, wherein said interpolating unit is operable to:

superimpose a plurality of cross-sectional dimension values over one another within a single pulsation cycle, the plurality of cross-sectional dimension values having been extracted over a plurality of pulsation cycles; and perform the interpolation using the superimposed cross-sectional dimension values to generate the interpolated cross-sectional dimension values.

5. The ultrasonic diagnostic device of claim 4, wherein said interpolating unit is operable to normalize the plurality of pulsation cycles before superimposing the plurality of cross-sectional dimension values by correcting time stamps associated with the plurality of cross-sectional dimension values so as to generate the single pulsation cycle.

6. The ultrasonic diagnostic device of claim 3, wherein:

said interpolating unit is operable to perform the interpolation using a plurality of data pairs that each contain a time stamp and a cross-sectional dimension value related to an ultrasound image in a first sectional view so as to generate interpolated cross-sectional dimension values related to the first sectional view; and said information generating unit includes:

an intersecting data obtaining unit operable to obtain a cross-sectional dimension value related to an ultrasound image in a second sectional view from said quantity extracting unit and to obtain a time stamp associated with the obtained cross-sectional dimension value from said time stamp generating unit, the first and second sectional views intersecting at a predetermined view;

a data specifying unit operable to specify a cross-sectional dimension value out of the interpolated cross-sectional dimension values related to the first sectional view, the specified interpolated cross-sectional dimension value being associated with a time stamp that indicates a same time as the time stamp obtained by said intersecting data obtaining unit; and a data generating unit operable to generate the diagnostic information by using the specified interpolated cross-sectional dimension value specified by said data specifying unit and the obtained cross-sectional dimension value obtained by said intersecting data obtaining unit.

7. The ultrasonic diagnostic device of claim 6, wherein:

said intersecting data obtaining unit is further operable to perform interpolation using a plurality of data pairs that each contain: (a) a cross-sectional dimension value related to the second sectional view, and (b) a time stamp associated with the cross-sectional dimension value in the data pair, and to generate an interpolated cross-sectional dimension value related to the second sectional view; and said data specifying unit is operable to specify a cross-sectional dimension value related to the first sectional view, the specified cross-sectional dimension value being associated with a time stamp indicating a same time as a time stamp associated with the interpolated cross-sectional dimension value related to the second section view generated by said intersecting data obtaining unit.

8. The ultrasonic diagnostic device of claim 6, wherein:
each time said image generating unit generates an ultrasound image in the second sectional view, said data generating unit generates diagnostic information; and
each time the diagnostic information is generated, said display unit displays the diagnostic information.

9. The ultrasonic diagnostic device of claim 6, wherein:
the subject-object is a left ventricle (LV) of a heart;
each cross-sectional dimension value is based on a contour of an endocardium of the LV; and
the diagnostic information shows an LV volume (LVV), which is obtained by substituting the cross-sectional dimension value into an approximate expression.

10. The ultrasonic diagnostic device of claim 9, wherein:
the cross-sectional dimension value indicates a length that specifies a slice related to the contour of the endocardium; and
the approximate expression is in accordance with the Modified Simpson method.

11. The ultrasonic diagnostic device of claim 10, further comprising a volume specifying unit operable to specify a maximum and a minimum of the volume in a pulsation cycle by using the volume shown in the diagnostic information.

12. The ultrasonic diagnostic device of claim 1, wherein the diagnostic information is a volume of the subject-object.

13. The ultrasonic diagnostic device of claim 1, further comprising:
a pulsation detecting unit operable to detect every pulsation related to the subject-object; and
a clock unit operable to measure an elapsed time from the detection of each pulsation;
wherein the time indicated by each time stamp is an elapsed time measured by said clock unit.

14. The ultrasonic diagnostic device of claim 13, wherein said interpolating unit is operable to:
superimpose a plurality of cross-sectional dimension values over one another within a single pulsation cycle, the plurality of cross-sectional dimension values having been extracted over a plurality of pulsation cycles; and
perform the interpolation using the superimposed cross-sectional dimension values to generate the interpolated cross-sectional dimension value.

15. The ultrasonic diagnostic device of claim 14, wherein said interpolating unit is operable to normalize the plurality of pulsation cycles before superimposing the plurality of cross-sectional dimension values by correcting time stamps associated with the plurality of cross-sectional dimension values so as to generate the single pulsation cycle.

16. An image processing device operable to generate and display diagnostic information related to a subject-object which is subject to examination by using successive ultrasound images each containing an image of the subject-object, the ultrasound images being generated based on reflection of ultrasound, wherein each ultrasound image is associated with a time stamp indicating a time at which the respective ultrasound image was generated, and each ultrasonic image includes a contour of a cross section of the subject-object, said image processing device comprising:
an extracting unit operable to extract, for each ultrasonic image, a respective cross-sectional dimension value based on the contour included in the respective ultrasonic image;
an interpolating unit operable to perform interpolation on at least two of the extracted cross-sectional dimension values so as to generate an interpolated cross-sectional dimension value corresponding to a time other than the times indicated by the time stamps associated with the at least two extracted cross-sectional dimension values, respectively;
an information generating unit operable to generate diagnostic information related to the whole subject-object in accordance with the extracted cross-sectional dimension values and the interpolated cross-sectional dimension value; and
a display unit operable to display the generated diagnostic information.

17. The image processing device of claim 16,
wherein said interpolating unit is operable to perform the interpolation a plurality of times so as to generate a respective plurality of interpolated cross-sectional dimension values, and said information generating unit is operable to generate the diagnostic information related to the whole subject-object in accordance with the extracted cross-sectional dimension values and the plurality of interpolated cross-sectional dimension values.

18. A program on a computer readable medium for use with a computer and operable to instruct the computer to function as an ultrasonic diagnostic device that generates and displays an ultrasound image containing an image of a subject-object in accordance with reflection of ultrasound, said program comprising:
an image generating part operable to instruct the computer to successively generate a plurality of ultrasonic images, wherein each ultrasonic image includes a contour of a cross section of the subject-object;
a quantity extracting part operable to instruct the computer to extract, for each respective ultrasonic image, a respective cross-sectional dimension value based on the contour included in the respective ultrasonic image;
a time stamp generating part operable to instruct the computer to generate, for each respective ultrasonic image, a respective time stamp indicating a time at which the respective ultrasonic image was generated, and to associate the respective time stamp with the respective cross-sectional dimension value as a respective data pair;
an interpolating part operable to instruct the computer to perform interpolation on at least two of the extracted cross-sectional dimension values so as to generate an interpolated cross-sectional dimension value corresponding to a time other than the times indicated by the time stamps contained in the data pairs that contain the at least two extracted cross-sectional dimension values, respectively;
an information generating part operable to instruct the computer to generate diagnostic information related to the whole subject-object in accordance with the extracted cross-sectional dimension values and the interpolated cross-sectional dimension value; and
a display part operable to instruct the computer to display the generated diagnostic information.

19. The program of claim 18, wherein said interpolating part is operable to instruct the computer to perform the interpolation a plurality of times so as to generate a respective plurality of interpolated cross-sectional dimension values, and said information generating part is operable to instruct the computer to generate the diagnostic information related to the whole subject-object in accordance with the extracted cross-sectional dimension values and the plurality of interpolated cross-sectional dimension values.

20. A program on a computer readable meduim for use with a computer and operable to instruct the computer to function as an image processing device that generates and displays diagnostic information related to a subject-object which is subject to examination by using successive ultrasound images each containing an image of the subject-object, the ultrasound images being generated based on reflection of ultrasound, wherein each ultrasound image is associated with a time stamp indicating a time at which the respective ultrasound image was generated, and each ultrasonic image includes a contour of a cross section of the subject-object, said program comprising:

- an extracting part operable to instruct the computer to extract, for each ultrasonic image, a respective cross-sectional dimension value based on the contour included in the respective ultrasonic image;
- an interpolating part operable to instruct the computer to perform interpolation on at least two of the extracted cross-sectional dimension values so as to generate an interpolated cross-sectional dimension value corresponding to a time other than the times indicated by the time stamps associated with the at least two extracted cross-sectional dimension values, respectively;
- an information generating part operable to instruct the computer to generate diagnostic information related to the whole subject-object in accordance with the extracted cross-sectional dimension values and the interpolated cross-sectional dimension value; and
- a display part operable to instruct the computer to display the generated diagnostic information.

21. The program of claim 20, wherein said interpolating part is operable to instruct the computer to perform the interpolation a plurality of times so as to generate a respective plurality of interpolated cross-sectional dimension values, and said information generating part is operable to instruct the computer to generate the diagnostic information related to the whole subject-object in accordance with the extracted cross-sectional dimension values and the plurality of interpolated cross-sectional dimension values.

* * * * *

UNITED STATES PATENT AND TRADEMARK OFFICE
CERTIFICATE OF CORRECTION

PATENT NO. : 6,730,032 B2
DATED : May 4, 2004
INVENTOR(S) : Masaki Yamauchi

It is certified that error appears in the above-identified patent and that said Letters Patent is hereby corrected as shown below:

Title page,
Item [73], Assignee, change "Matsushita Electric Industrial Co., Osaka (JP)" to
-- Matsushita Electric Industrial Co., Ltd. Osaka (JP) --.
Item [57], ABSTRACT,
Line 1, delete "(116)" after "unit".
Line 3, delete "(101)" after "unit".
Line 4, delete "(102)" before ",".
Line 4, delete "(110)" after "unit".
Line 6, delete "(112)" after "unit".
Line 7, delete "(113)" after "unit".
Line 8, delete "(112)" after "unit".
Line 11, delete "(114)" after "unit".
Line 14, delete "(115)" after "unit".

Signed and Sealed this

Twenty-third Day of November, 2004

JON W. DUDAS
*Director of the United States Patent and Trademark Office*